(12) United States Patent
Trauner et al.

(10) Patent No.: US 11,033,350 B2
(45) Date of Patent: Jun. 15, 2021

(54) MULTI-LAYER PRE-DRAPE APPARATUS AND PROCESS

(71) Applicant: Work Fluidics, San Francisco, CA (US)

(72) Inventors: Kenneth B Trauner, San Francisco, CA (US); Josef Gorek, Ross, CA (US)

( * ) Notice: Subject to any disclaimer, the term of this patent is extended or adjusted under 35 U.S.C. 154(b) by 234 days.

(21) Appl. No.: 16/345,926

(22) PCT Filed: Nov. 2, 2017

(86) PCT No.: PCT/US2017/059798
§ 371 (c)(1),
(2) Date: Apr. 29, 2019

(87) PCT Pub. No.: WO2018/085594
PCT Pub. Date: May 11, 2018

(65) Prior Publication Data
US 2020/0060781 A1    Feb. 27, 2020

Related U.S. Application Data

(63) Continuation-in-part of application No. PCT/US2016/059998, filed on Nov. 2, 2016.

(51) Int. Cl.
*A61B 46/20* (2016.01)
*A61B 46/27* (2016.01)
(Continued)

(52) U.S. Cl.
CPC ............ *A61B 46/20* (2016.02); *A61B 17/135* (2013.01); *A61B 46/00* (2016.02); *A61B 46/27* (2016.02);
(Continued)

(58) Field of Classification Search
CPC .............. A61B 46/40; A61B 2046/201; A61B 2046/205; A61B 2046/234; A61B 2046/236; A61B 19/08; A61B 19/087; A61B 19/10; A61B 19/12; A61B 2019/084; A61B 2019/08; A61B 46/00; A61G 13/0054; A61G 13/04; A61G 13/1275; A61G 13/1245; A61G 13/122; A61G 13/08; A61G 7/0526; A61G 7/0504; A61F 2013/15073; A61F 2013/15008; A61F 5/379
See application file for complete search history.

(56) References Cited

U.S. PATENT DOCUMENTS

2014/0219865 A1\*  8/2014  Reese .................... A61B 46/00
                                                                                     422/28

\* cited by examiner

*Primary Examiner* — Ophelia A Hawthorne
(74) *Attorney, Agent, or Firm* — Staniford Tomita LLP

(57) ABSTRACT

A multi-layer pre-drape apparatus is applied to a patient before the patient is moved into the operating room. The multi-layer pre-drape apparatus includes a lower layer with a center aperture and an upper layer that covers the aperture. The multi-layer pre-drape apparatus can be placed on a sterilized area of the patient to maintain the cleanliness of the incision area. Alternatively, the multi-layer pre-drape apparatus can be placed on the patient and sterilization fluid can be applied to the skin of the patient through the aperture. The patient can then be moved into the operating room and the upper layer of the multi-layer pre-drape can be removed to expose the sterilized area of the patient in the aperture. Additional drapes can be added to the pre-drape apparatus.

13 Claims, 32 Drawing Sheets

(51) Int. Cl.
*A61B 46/00* (2016.01)
*A61B 17/135* (2006.01)
*A61M 19/00* (2006.01)
*A61B 90/80* (2016.01)
*A61B 46/23* (2016.01)

(52) U.S. Cl.
CPC .............. *A61B 46/40* (2016.02); *A61B 90/80* (2016.02); *A61M 19/00* (2013.01); *A61B 2046/201* (2016.02); *A61B 2046/205* (2016.02); *A61B 2046/236* (2016.02)

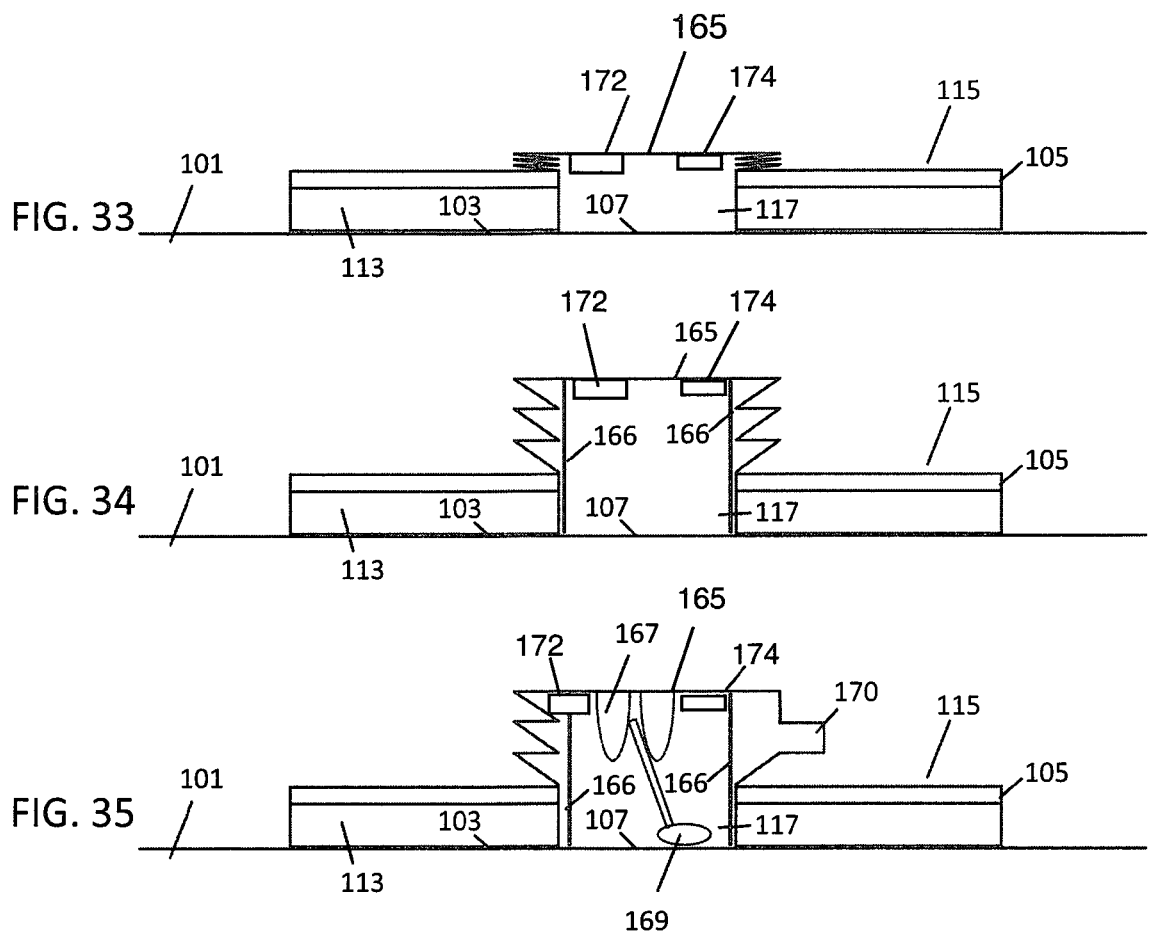
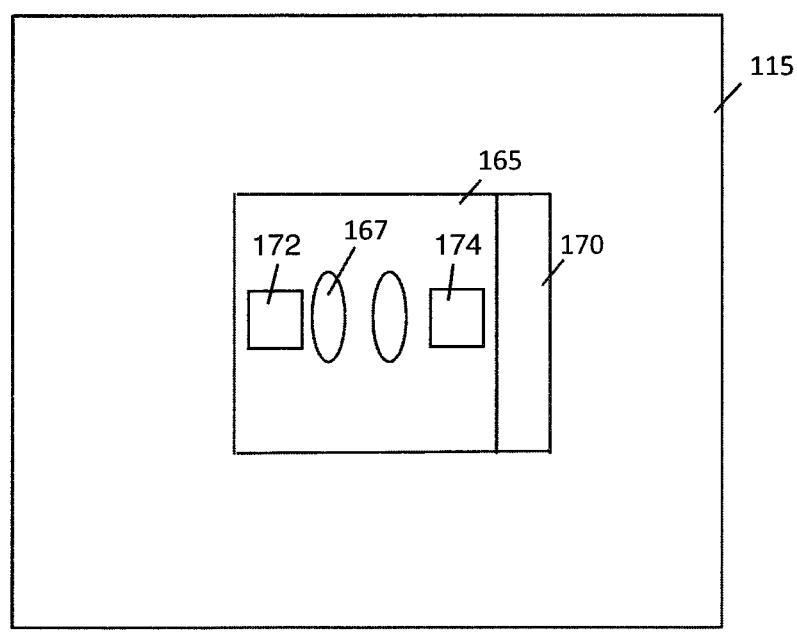

MULTI-LAYER PRE-DRAPE APPARATUS AND PROCESS

CROSS REFERENCE TO RELATED APPLICATIONS

This patent application claims priority to PCT Application No. PCT/US16/59998, "Multi-Layer Drape Apparatus And Process" which was filed on Nov. 2, 2016 and is hereby incorporated by reference in its entirety.

BACKGROUND

Patient surgery can be very expensive. By making surgeries more time efficient, the costs of surgeries can be reduced. Time in the operating room (OR) is expensive so reducing the time each patient needs in the OR without compromising the medical procedures in any way can reduce surgical costs. Much of this expensive time spent in the OR is due to prepping and draping the patient prior to their surgery. The OR is a specialized sterile environment. In the OR environment, preparing or prepping of the surgical site is performed by OR personnel. The prepping process may include: applying an anti-bacterial solution to the skin of the patient, allowing the solution to dry on the skin and then applying draping materials to the skin of the patent.

Skin is a non-sterile tissue with a high bacterial count. Prepping of the skin refers to the treatment of the skin with specialized solutions that aim to reduce the bacterial count. The reduction of the bacterial count in the skin is directly proportional to the duration of exposure to the cleansing solutions. The final step of prepping requires that the solution on the skin be allowed to dry. Typical drying time may take several minutes.

At the completion of prepping, the OR personnel then drapes the surgical site. Draping consists of applying drape material in layers surrounding the incision site. Frequently, adhesive drapes are also applied to the incision site. Adhesive drapes such as 3M Loban are placed on the skin adjacent to the planned incision area so the drapes can prevent migration of bacterial contamination into the surgical site.

By current protocol embodiments, patients are admitted to a pre-surgical unit prior to surgery. In the pre-surgical unit, the patients are processed and prepared before being transferred into the OR. Preparation of the patient includes the processing of the patient by nurses, physicians and administrative staff. Processes include interviewing and examining the patient and may also include undressing the patient from street clothes to place him or her in a surgical gown. As such, the pre-surgical unit is a non-sterile environment.

In some embodiments, patients are transferred to sub-sterile settings where anesthetic procedures are performed. These procedures include line placements or anesthetic blocks such as spinal or regional anesthesia. The costs of time for procedures performed in the pre-surgical unit can be substantially lower than the costs of time for procedures performed in the OR.

The prepping and draping of the patient consumes valuable time in the OR at great expense to the hospital. For example, for total limb joint surgical procedures, it may commonly take more than thirty minutes from the time the patient arrives in the OR until the surgeon makes the first incision for the surgical procedure.

Current financial cost pressures are forcing hospitals to expedite work flows in the OR. This invention is directed towards new draping devices, technologies and methods that allow for the safe sterile and prepping of surgical sites outside of the OR environment as many hospitals do not have space available for sub-sterile processing.

What are needed are methods and devices for safe sterile prepping and draping of patients outside the OR in order to minimize the processing of the patient in the OR prior to the first surgical incision. The present invention also describes devices that are modified for different regions of the body to address an array of surgical procedures.

SUMMARY OF THE INVENTION

The present invention is directed towards a multi-layer pre-drape apparatus and method. Rather than sterilizing an incision area of a patient in an operating room (OR), an area of a patient can be sterilized outside of the OR and a multi-layer pre-drape apparatus can be used to maintain the sterilization before the patient is moved into the OR. Once the patient is within the OR, an upper layer of the multi-layer pre-drape apparatus can be removed to expose the sterilized area of the patient. Drapes can then be applied to the patient and the surgical procedure can be performed.

In an embodiment, the multi-layer pre-drape apparatus can include an upper layer and a lower layer that has an aperture. The upper layer can be adhesively secured to the lower layer and the upper layer can cover the entire lower layer and the aperture. In different embodiments, the pre-drape apparatus can have various features such as integrated: drapes, sterilization fluids, sponge, storage areas, shelves, fluid ports, needle ports, etc. The pre-drape apparatus can be stored in a hermetically sealed sterile package that can be opened when the pre-drape apparatus is ready to be used.

An area of a patient can be sterilized by scrubbing the area with a sterile solution using a sponge or other mechanism. The sterile solution can then be allowed to dry on the area of the patient. The pre-drape apparatus can be removed from its packaging. The lower surface of the lower layer can have an adhesive surface. An adhesive release liner can be removed from the lower surface and the lower layer can be placed over the sterilized area of the patient with the aperture of the lower layer over the incision area. Pressure can be applied to the pre-drape apparatus to secure the adhesive to the skin of the patient.

In an embodiment, a pre-drape apparatus can be adhesively bonded to the patient and a sterile solution can be used to clean the area of the patient within the aperture. The sterile solution can be in a packet contained within the pre-drape apparatus with a sponge or alternatively, the sterile solution may be injected through the upper layer into the aperture area. Once attached to the patent, the sterile solution can be used to sterile the patient. In an embodiment, the inner surface of the upper layer can be made of a sponge material that can absorb the sterilization solution and be pressed against the patient to clean the skin within the aperture of the lower layer.

In other embodiments, pre-drape apparatus can be a flexible structure that can surround a limb of a patient to effectively contain the limb within a sealed bag. The pre-drape apparatus can include a sheet of material that has an adhesive around a perimeter portion of the sheet. A limb can be placed over the sheet and the sheet can surround the limb with the adhesive portions of the sheet forming a seal around the limb. The adhesive can also surround a proximal portion of the limb. In other embodiments, the pre-drape apparatus can be a flexible bag having an opening that can have an adhesive seal. The limb can be placed into the opening and once fully inserted, the adhesive can be secured around the limb.

A sterile solution can be used to clean the limb within the double sealed bag. In an embodiment, the inner surface of the sheet can function like a sponge, which can absorb the sterile solution and can be pressed against the limb to perform the sterilization with air pressure between the inner and outer bags. Once the limb has been sterilized, the sealed bag can be coupled to a ventilation system which can direct air into the bag. Air can flow into the bag in an area adjacent to the incision area so that the sterilization solution flows away from the incision area. The air and excess sterilization solution can flow out one or more air outlets coupled to the bag. The air flow can dry the sterilization fluid on the limb. Once dry, the patient can be moved into the OR and a portion of the bag over the incision area can be removed. Drapes can be coupled to the bag before performing the surgery. In an embodiment, the sterilization process can be an automated process which does not require manual scrubbing of the limb.

BRIEF DESCRIPTION OF THE DRAWINGS

FIG. 33 illustrates a side view of an embodiment of a multi-layered pre-drape apparatus with a tent in a collapsed position on a patient.

FIG. 34 illustrates a side view of an embodiment of a multi-layered pre-drape apparatus with a tent in an expanded position on a patient.

FIG. 35 illustrates a side view of an embodiment of a multi-layered pre-drape apparatus with a tent in an expanded position with additional features on a patient.

FIG. 36 illustrates a top view of an embodiment of a multi-layered pre-drape apparatus with a tent with additional features.

FIGS. 75-77 illustrate a front view of a tourniquet having a bladder and a strap with a ratchet tension mechanism.

DETAILED DESCRIPTION

Figure 1:
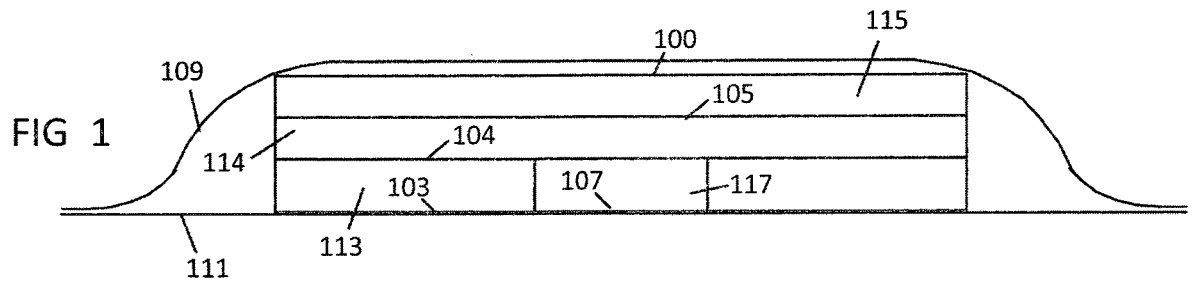
FIG. 1 illustrates a side view of a three layer embodiment of a pre-drape apparatus in a sterile package.

In an embodiment, a "pre-drape" apparatus can be applied to a patient prior to a surgical procedure. An area of surface skin on the patient can be sterilized with a sterile solution such as: aqueous iodophor, aqueous CHG, alcohol iodophor, alcohol CHG, pHisoHex, pHisoDerm, iodine and any other suitable antiseptic solution. Alcohols have rapid activity when applied to the skin, but alone do not have a persistent, cumulative activity; however, when combined with another antiseptic agent persistent, cumulative activity results. Therefore, a sterile solution can be a combination of alcohol and other antiseptic agent (alcohol-based solution). Alcohol-based solutions can have a greater antimicrobial activity as compared to other solutions. Alcohol-based solutions can lower the microbial count on the skin more effectively than other solutions. For example, alcohol-based solutions that contain 0.5% to 1% chlorhexidine gluconate have been found to have a persistent antimicrobial activity that is equal to, or greater, than that of CHG alone. Other effective sterile scrubbing agents include: chlorhexidine gluconate, iodophors, and triclosan.

The sterile solution can be applied to the skin of the patient to sterilize the skin around the surgical site. The sterility of the patient's skin can be proportional to the amount of time of exposure to the sterile solution. Thus, the skin will be more sterile when exposed longer to the sterile solution. As discussed, OR time is very expensive. So if a substantial amount of time is required to sterilize a patient in the OR, this use of time will be very expensive. In order to reduce the sterilization OR costs, it is not uncommon for the sterile solution exposure time to be minimized. Thus, the sterilization process may not be optimized in many surgical procedures. This lack of sterility is problematic. Surgical site infection (SSI) complicates an estimated 5% of all clean-contaminated operations performed annually in US hospitals and accounts for the most common nosocomial infection in surgical patients. Patients who develop SSI have longer and costlier hospitalizations and are more likely to spend time in an intensive care unit (ICU), are 5 times more likely to be readmitted, and are twice as likely to die.

In an embodiment of the present invention, the sterility of the patient can be substantially improved by performing the sterilization of the patient prior to moving the patient into the OR. For example, the sterilization of the patient can be performed in an ambulatory surgical center (ASC) prior to moving the patient into the OR. Thus, the inventive process of applying the sterile solution to the patient outside the OR has the benefits of: improving the sterility of the surgical field, reducing the likelihood of surgical site infection and reducing the costs of the surgery. Since the patient's skin is sterilized outside the OR, the surgical procedure can be performed more quickly and no time is consumed in the OR by the application of sterile solution to the patient.

In some embodiments, the sterile solution is allowed to dry on the patient and a pre-drape apparatus can be secured to the patient over the sterilized skin area. With reference to FIG. 1, a side view of a pre-drape apparatus 100 in a sterile package is illustrated. The pre-drape apparatus 100 may include an upper layer 115, a middle layer 114 and a lower layer 113. The sterile package can include an upper package 109 and a lower package 111 that maintains the sterility of the pre-drape apparatus 100 until use. First a sterile adhesive 105 can be applied in the interface between the lower surface of the upper layer 115 and the upper surface of the lower layer 113 and a second sterile adhesive 103 can be applied to the lower surface of the lower layer 113. The lower package 111 may have an adhesive release film that is in physical contact with a sterile adhesive 103 on the lower surface of the lower layer 113.

Figure 2:
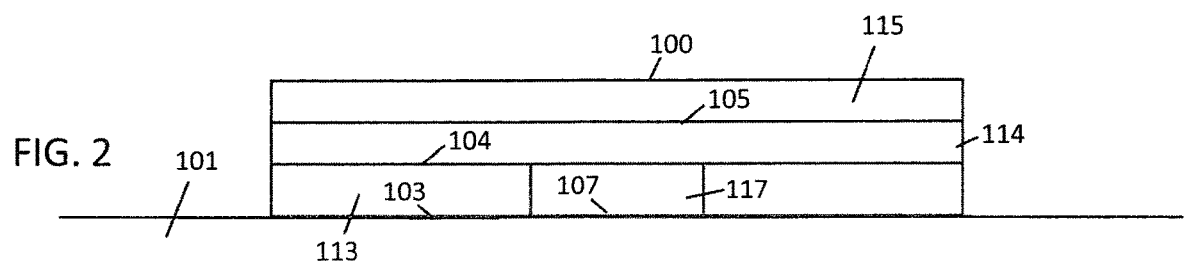
FIG. 2 illustrates a side view of a three layer embodiment of a pre-drape apparatus having an aperture on a patient.

With reference to FIG. 2, the pre-drape apparatus 100 has been removed from the upper package 109 and placed on the skin 101 of the patient. The lower package release film has been separated from the adhesive 103 on the lower surface of the lower layer 113. When the sterile release film is removed, the sterile adhesive 103 is exposed and can be secured to the patient. When placed on the patient outside the OR, the outer upper surface of the upper layer 115 can be unsterile. However, all other surfaces including the lower surface of lower layer 113 and the interface 105 between the lower surface of the upper layer 115 and the upper surface of the lower layer 113 can be sterile.

The multi-layered pre-drape apparatus 100 can have three or more layers 113, 114, 115. In these embodiments, the interfaces 104, 105 between the different layers 113, 114, 115 can be sterile adhesives. The different layers 113, 114, 115 can be attached to each other with different adhesive strengths that can be progressively stronger with position in the multi-layer stack. The highest strength adhesive 103 can be between the lowest layer 113 and the skin 101, while the weakest strength adhesive 105 can be between the upper most or outer most layer 115 and the second outermost layer 114. In these embodiments, the multi-layered pre-drape 100 can be configured to allow a user to sequentially remove the outer drape layer 115 and then the middle drape layer 113 and then the inner drape layer 113. More specifically, when the upper layer 115 is pulled for removal, all of the adhesive layers 103, 104, 105 will be exposed to the same tensile forces. However, because the upper adhesive layer 105 is the weakest pull off adhesion, only the upper layer 115 will be removed when the tension force exceeds the pull off adhesion. As the layers 115, 114, 113 are sequentially removed, more force may be required to exceed the increasing pull off adhesion forces.

In an embodiment, the pull off adhesion of each adhesive layer 103, 104 and 105 can be quantified as in units of force/area such as pounds per square inch. Thus, the upper adhesive 105 between the upper layer 115 and the lower layer 113 may have a pull of adhesion of 0.5 PSI or less which is lower than the middle adhesive 104 which may have a pull off adhesion of 0.75 PSI or less and the lower adhesive 103 between the skin and the lower layer 113 which may have a pull off adhesion of 1.0 PSI or less.

Table 1 is an example of adhesive strengths for a 2 layer pre-drape structure and Table 2 is an example of adhesive strengths for a 3 layer pre-drape structure. In other embodiments, a drape apparatus can have any number of layers with the described progressive change in pull off adhesive strengths. In these tables examples of the pull off adhesion values are listed. In other embodiments, any other suitable pull off adhesion values can be used as long as the different adhesive layers have progressively stronger pull off adhesion strengths. The upper limits of pull off adhesion should allow the lowest layer to be removed from the patient's skin without causing any damage to the skin.

In an embodiment, the adhesives may be more strongly bonded to the lower surfaces of the multiple different layers. When each layer is removed, all of the newly adhesive material that has been exposed can be removed as well. This concept can be similar to a "post it" where the adhesive does not leave the paper or tape. This feature will leave a clean layer on the newly exposed upper layer. By not having any adhesive remaining on the exposed upper surfaces of the layers, the surgical field will be free of adhesive materials. In some embodiments, an adhesive solvent can be used to dissolve the adhesive below the lowest layer. This dissolving process can be useful when a drape needs to be removed from a patient with sensitive, weak and/or thin skin. Once the adhesive has been removed, the layer can be pulled from the skin without causing any tearing damage to the skin.

TABLE 1

| Interface | Pull Off Adhesion |
| --- | --- |
| Layer 1 to Layer 2 | 1-2 PSI |
| Layer 2 to Skin | 4-5 PSI |

TABLE 2

| Interface | Pull Off Adhesion |
| --- | --- |
| Layer 1 to Layer 2 | 1-2 PSI |
| Layer 2 to Layer 3 | 3-4 PSI |
| Layer 3 to Skin | 5-6 PSI |

In an embodiment, a layer removal process can be performed to avoid damage to the skin 101 of the patient. A designated corner can be pulled away from the underlying layer 114 in a progressive peeling motion. The adhesive removal can proceed across the contact area so that only a small area of adhesive is being removed at any time. Because only a small area is being pulled away at one time, the force required to remove each layer may not be more than a pound or less and the pressure applied to the skin is minimal. In an embodiment, the designated removal starting corner can be marked or designated as a tab. The adhesive in the removal corner can be weaker or omitted so that the starting corner can be easily peeled away. In an embodiment, the adhesive 105 can be secured to the upper layer 115 so that when the upper layer 115 is pulled away from the middle layer 114, the adhesive 105 is also removed. The upper surface of the middle layer 114 can have a release film material surface such as wax paper or plastic. In other embodiments, it can be desirable to have the adhesive 105 remain on the middle layer 113 so that added drapes can be secured to the lower layer 113.

Figure 3:
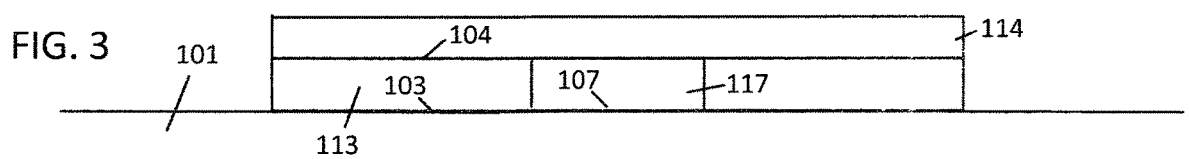
FIG. 3 illustrates a side view of two layers of a pre-drape apparatus having an aperture on a patient.
Figure 4:
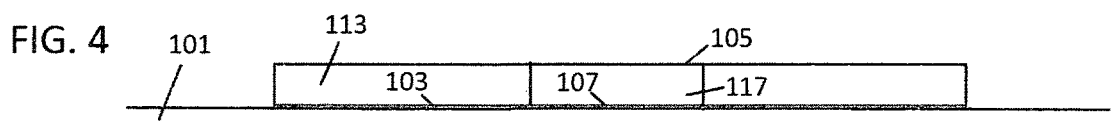
FIG. 4 illustrates a side view of lower layer of a pre-drape apparatus having an aperture on a patient.

With reference to FIG. 3, the patient may be moved into the OR and upper layer which is unsterile has been removed. The sterile middle layer 114 is now exposed which covers the aperture 117. The adhesive 104 can be secured to the middle layer 114 so that when the middle layer 114 is pulled away from the lower layer 113, the adhesive 104 is also removed. The upper surface of the lower layer 113 can have a release film material. With reference to FIG. 4, the patient is in the OR and the middle layer 114 has been removed. The lower layer 113 and the skin area 107 within the aperture 117 are exposed.

In addition to having different adhesive strengths, the different layers can be color coded to illustrate the sterility of the pre-drape apparatus 100. As discussed, the pre-drape apparatus 100 can be applied to the patient outside of the OR. Thus, the upper surface of the upper layer 115 is non-sterile. The patient can be moved into the OR before the upper layer 115 is removed and the upper layer of the middle layer 114 can be sterile. When the surgeon is ready to cut the patient, the middle layer 114 can be removed and the upper lower layer 113 can also be sterile. In an embodiment, the sterile and non-sterile status of the different layers can be identified visually. For example, a non-sterile layer can be designated with a first color such as yellow and a sterile layer can be designated with a second color such as green. In the illustrated example, the upper surface of the upper layer 115 can be a first color (yellow) to designate that it is non-sterile. The upper surfaces of the middle layer 114 and the lower layer 113 can be green to indicate that these surfaces are sterile. In other embodiments, the upper surfaces of the different layers can be marked with text which can simply state, "sterile" or "non-sterile." By looking at the colors of the layers, the OR staff can distinguish the non-sterile upper layer 115 from the sterile middle layer 114.

Figure 5:
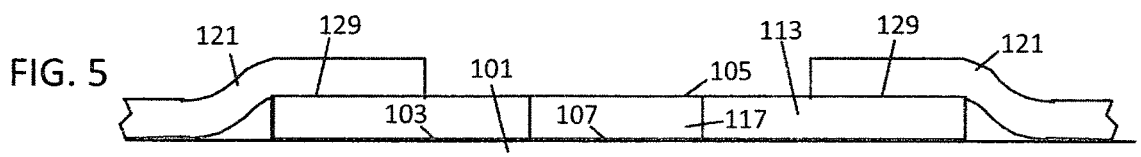
FIG. 5 illustrates a side view of lower layer of a pre-drape apparatus on a patient with additional drapes attached to the lower layer.

With reference to FIG. 5, in some embodiments, it can be desirable to have the adhesive remain on the upper surface of the lower layer 113 so that added drapes 121 can be secured to the lower layer 113 around the aperture 117. Alternatively, an adhesive can be placed on the contact areas of the added drapes 121 and the lower layer 113 to create a seal between at the areas 129 where the drapes 121 and the lower layer 113 overlap. The added drapes 121 can then rest on the skin 101 of the patient around the lower layer 113.

Figure 6:
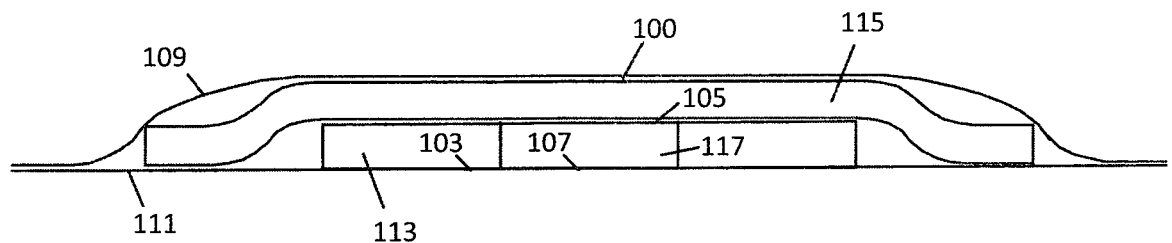
FIG. 6 illustrates a side view of a two layer embodiment of a pre-drape apparatus in a sterile package.

While the pre-drape apparatus shown in FIGS. 1-4 illustrate layers that are all the same size, in other embodiments, the layers of the pre-drape apparatus can have various sizes. FIG. 6 illustrates a sterile two layer pre-drape apparatus 100 in a package that includes the upper package 109 and a lower package 111 which may have a release film attached to the adhesive 103 on the lower surface of the lower layer 113 and the adhesive 105 on the lower layer of the upper layer 115. In this example, the upper layer 115 is larger than the lower layer 113 and overlaps the outer perimeter of the lower layer 113.

Figure 7:
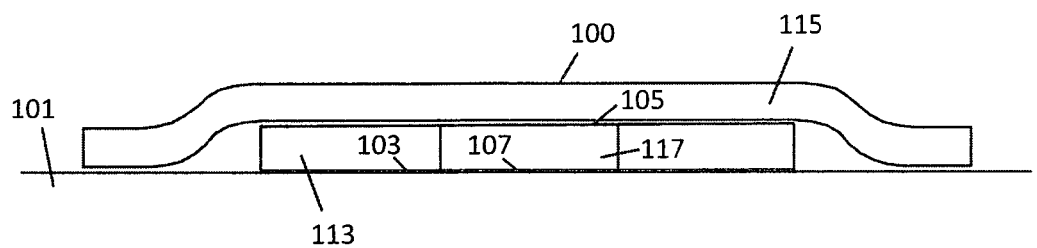
FIG. 7 illustrates a side view of a two layer embodiment of a pre-drape apparatus having an aperture on a patient.
Figure 8:
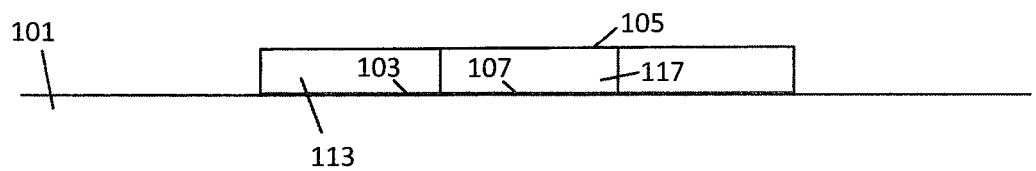
FIG. 8 illustrates a side view of a lower layer of a pre-drape apparatus having an aperture on a patient.
Figure 9:
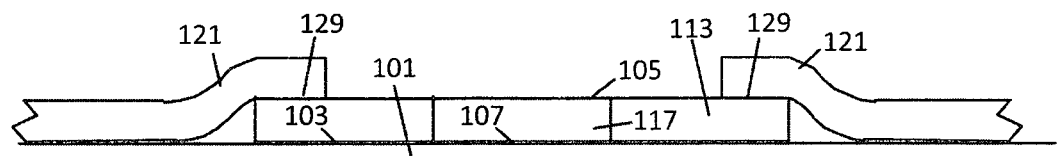
FIG. 9 illustrates a side view of a lower layer of a pre-drape apparatus with additional drapes attached around the aperture on a patient.

With reference to FIG. 7, the pre-drape apparatus 100 has been removed from the package and placed on the skin 101 of the patient with the aperture 117 over the incision area of the skin 107 outside of the OR. The adhesive 103 holds the lower layer 113 to the skin 101 and the adhesive 105 holes the upper layer 115 to the skin 101 around the perimeter of the lower layer 113. With reference to FIG. 8, the patient can be moved into the OR and the upper layer has been removed. The lower layer 113 and the incision area of the skin 107 are exposed. With reference to FIG. 9, it can be desirable to keep the adhesive on the upper layer of the lower layer 113. Additional drapes 121 can be placed on the lower layer 113. The adhesive 105 can create a seal between at the areas 129 where the drapes 121 and the lower layer 113 contact each other and overlap.

Figure 10:
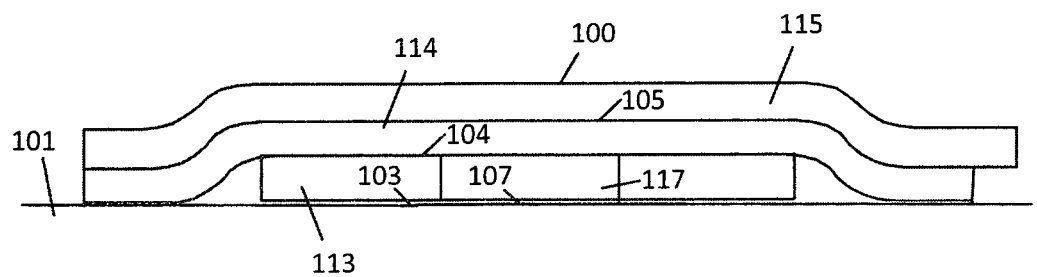
FIG. 10 illustrates a side view of a three layer embodiment of a pre-drape apparatus on a patient.
Figure 11:
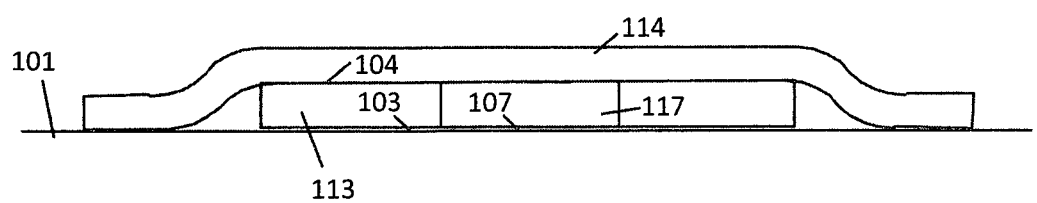
FIG. 11 illustrates a side view of a middle layer and a lower layer of a pre-drape apparatus on a patient.
Figure 12:
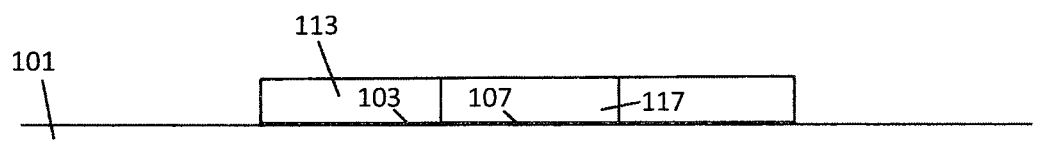
FIG. 12 illustrates a side view of a lower layer of a pre-drape apparatus having an aperture on a patient.

With reference to FIG. 10, a three layer pre-drape apparatus 100 is illustrated. In this embodiment, the upper layer 115 and the middle layer 114 can be larger than the lower layer 113. The upper layer 115 can be held to the middle layer 114 with an adhesive 105 and the middle layer 114 can be held to the lower layer 113 with an adhesive 104 that can have a lower bonding strength as described above. The three layer pre-drape apparatus 100 can be placed on the skin 101 of the patient outside of the OR. With reference to FIG. 11, the upper layer 115 has been removed and the middle layer 114 is exposed. With reference to FIG. 12, the patient can be moved into the OR and the middle layer 114 is removed to expose the lower layer 113 and the incision area of the skin 107 in the aperture 117.

Figure 13:
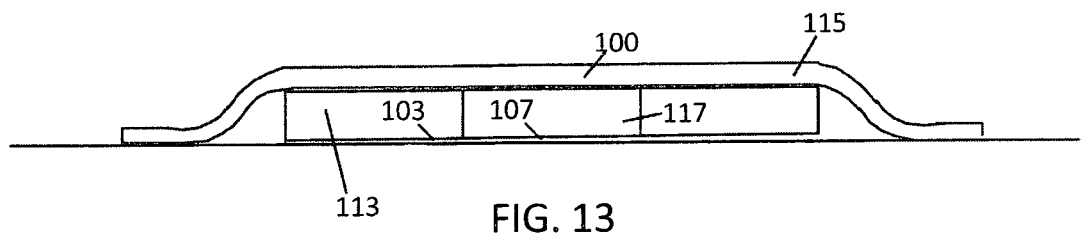
FIG. 13 illustrates a side view of a two layer embodiment of a pre-drape apparatus having an aperture on a patient.

With reference to FIG. 13, another embodiment of a two layer pre-drape apparatus 100 is illustrated having a lower layer 113 and an upper layer 115 that is larger than the lower layer 113 and extends over the perimeter of the lower layer 113. In the illustrated embodiment, the pre-drape apparatus 100 can be placed on a patient with the aperture 117 over an incision area of the skin 107 outside the OR. The upper layer 115 is exposed and non-sterile. The patient can then be moved into the OR and the upper layer 115 can be removed to expose the lower layer 113, the aperture 117 and the incision area of the skin 107.

Figure 14:
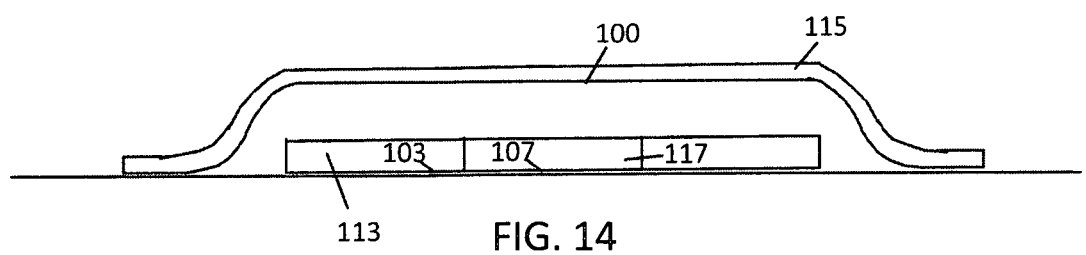
FIG. 14 illustrates a side view of two spaced apart layers of a pre-drape apparatus having an aperture on a patient.

With reference to FIG. 14, in an embodiment, it is possible to have a multi-layer pre-drape apparatus 100 where the upper layer 115 and the lower layer 113 are not in direct physical contact. In the illustrated embodiment, the upper layer 115 and the lower layer 113 can be separated by a space. The upper layer 115 can be adhesively bonded to the skin to form a seal around the lower layer 113 to maintain the sterility of the lower layer 113 and the skin under the upper layer 115. The lower layer 113 can be coupled to the skin with an adhesive 103. In this embodiment, an adhesive may not exist in the area between the upper layer 115 and the lower layer 113. In an embodiment, the space can be created with sterile gas pressure, which can be injected between the upper layer 115 and the lower layer 113. After the patient is moved into the OR, the upper layer 115 can be removed to expose the lower layer 113, the aperture 117 and the incision area of the skin 107.

Figure 15:
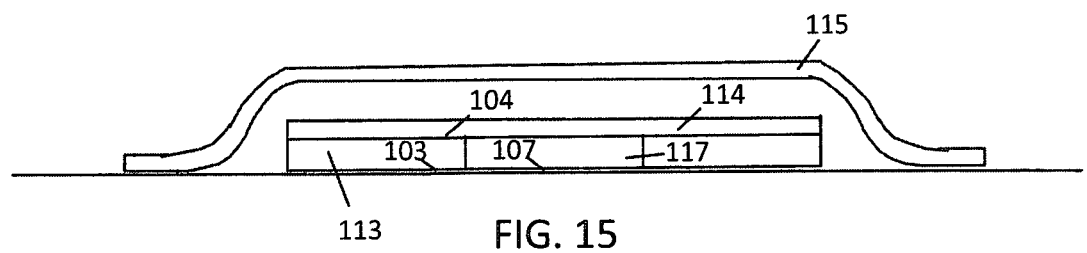
FIG. 15 illustrates a side view of a three layer embodiment of a pre-drape apparatus where the upper layer and the middle layer are separated.

With reference to FIG. 15, the multi-layer pre-drape apparatus can include a lower layer 113 that is held to the middle layer 114 with an adhesive 104. The upper layer 115 and the middle layer 114 can be separated by a space. The upper layer 115 can be adhesively bonded to the skin to form a seal around the middle layer 114 and the lower layer 113 to maintain the sterility of the middle layer 114 and the lower layer 113 and the skin under the upper layer 115. The lower layer 113 can be coupled to the skin with an adhesive 103. In this embodiment, an adhesive may not exist in the area between the upper layer 115 and the middle layer 114. In an embodiment, the space can be created with sterile gas pressure, which can be injected between the upper layer 115 and the middle layer 114. The upper layer 115 can be removed to expose the middle layer 114, the lower layer 113, the aperture 117 and the incision area of the skin 107. After the patient is moved into the OR, the middle layer 114 can be removed to expose the lower layer 113, the aperture 117 and the incision area of the skin 107.

Figure 16:
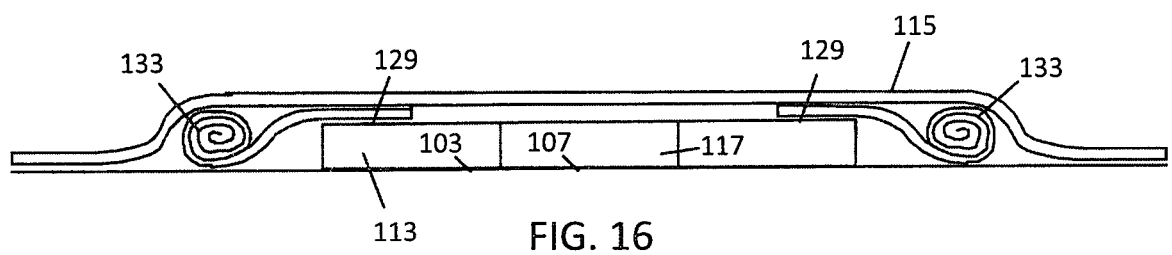
FIG. 16 illustrates a side view of a three layer embodiment of a pre-drape apparatus where the middle layer includes a rolled portion.

With reference to FIG. 16, the multi-layer pre-drape apparatus can include an upper layer 115, a rolled drape layer 133 and a lower layer 113. The upper layer 115 can be larger than the lower layer 113 and the rolled drape layer 133 can be larger than the upper layer 115 in its expanded state but small in area in a rolled state (as shown). The pre-drape apparatus can be placed on the patient outside of the OR with the aperture 117 of the lower layer 113 over an incision area of the skin 107. An adhesive 103 can hold the lower layer 113 to the patient. When the patient is moved into the OR, the upper layer 115 can be removed and the rolled drape layer 133 can be unrolled. The lower layer 113, the aperture 117 and the incision area of the skin 107 can also be exposed.

Figure 17:
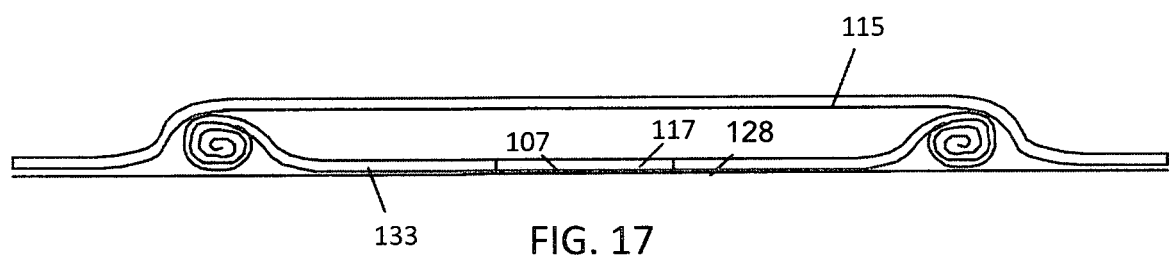
FIG. 17 illustrates a side view of a two layer embodiment of a pre-drape apparatus where the lower layer includes a rolled portion.

With reference to FIG. 17, in an embodiment, the multi-layer pre-drape apparatus can include an upper layer 115 and a rolled drape 133 that has an aperture 117 that surrounds an incision area of the skin 107 of the patient. The rolled drape 113 can be secured to the patient with an adhesive 128. When the patient is moved into the OR, the upper layer 115 can be removed and the rolled drape layer 133 can be unrolled. The aperture 117 and the incision area of the skin 107 can also be exposed.

Figure 18:
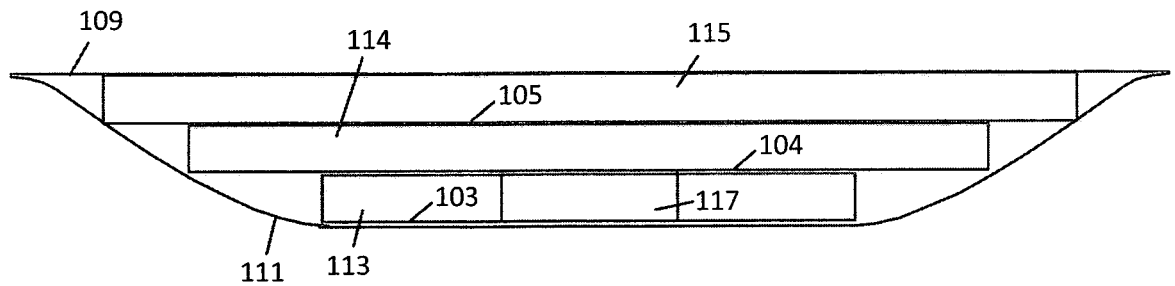
FIG. 18 illustrates a side view of a three layer embodiment of a pre-drape apparatus where the upper layer is larger than the middle layer which is larger than the lower layer in a sterile package.
Figure 19:
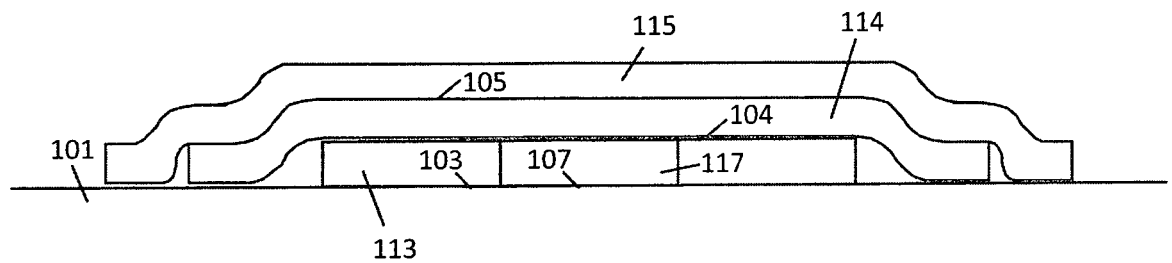
FIG. 19 illustrates a side view of a three layer embodiment of a pre-drape apparatus where the upper layer is larger than the middle layer which is larger than the lower layer placed on a patient.
Figure 20:
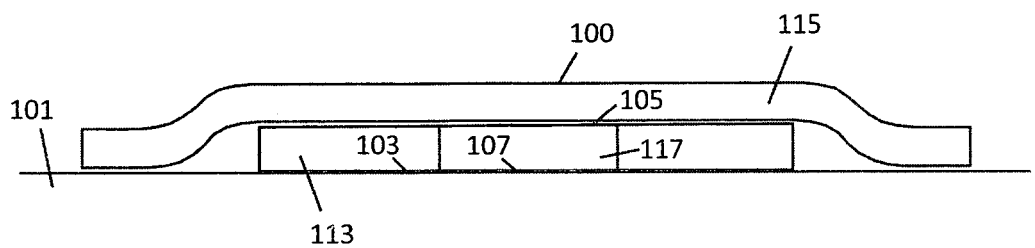
FIG. 20 illustrates a side view of a middle layer and a lower layer on a patient.
Figure 21:
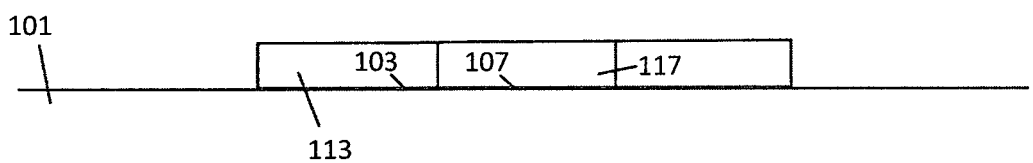
FIG. 21 illustrates a side of a lower layer on a patient.
Figure 22:
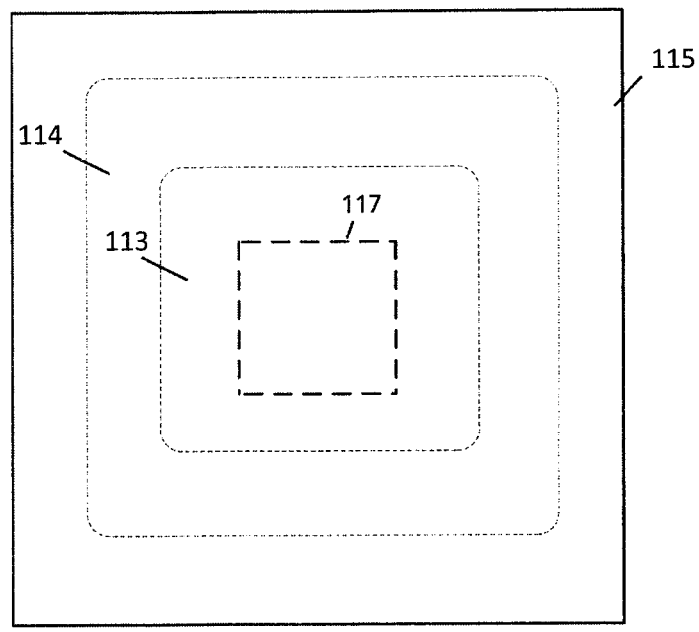
FIG. 22 illustrates a top view of a three layer embodiment of a pre-drape apparatus where the upper layer is larger than the middle layer which is larger than the lower layer.

With reference to FIG. 18, a multi-layer pre-drape apparatus in a sterile package having an upper package 109 and a lower package 111 is illustrated. In this embodiment, the upper layer 115 is larger than the middle layer 114 which is larger than the lower layer 113 which includes an aperture 117. With reference to FIG. 19, the multi-layer pre-drape apparatus is removed from the sterile package and placed on the skin 101 of a patient with the aperture 117 over the incision area of the skin 107. An adhesive 104 can secure the middle layer 114 to the skin 101 and form a seal around the lower layer 113 and an adhesive 105 can secure the upper layer 115 to the skin and form a seal around the middle layer 114. With reference to FIG. 20, the upper layer 115 has been removed to expose the middle layer 114. With reference to FIG. 21, the patient has been moved into the OR and the middle layer 114 can be removed to expose the lower layer 113, the aperture 117 and the incision area of the skin 107. FIG. 22 illustrates a top view of the multi-layer pre-drape apparatus showing that the upper layer 115 is larger than the middle layer 114 which is larger than the lower layer 113 which includes an aperture 117.

Figure 23:
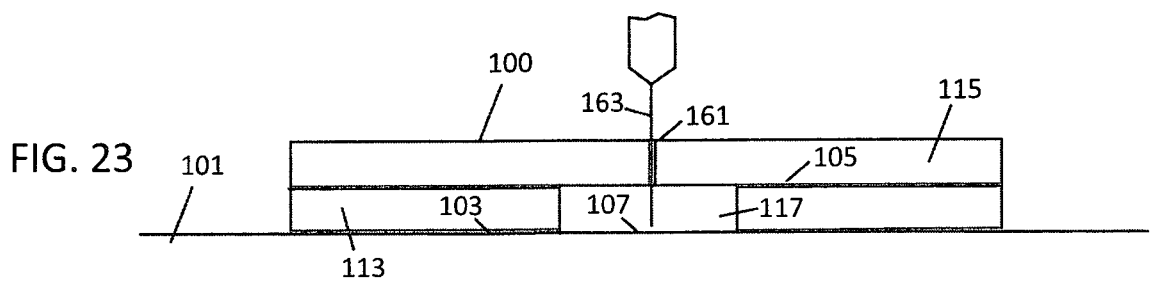
FIG. 23 illustrates a side view of a pre-drape apparatus having a needle port.
Figure 24:
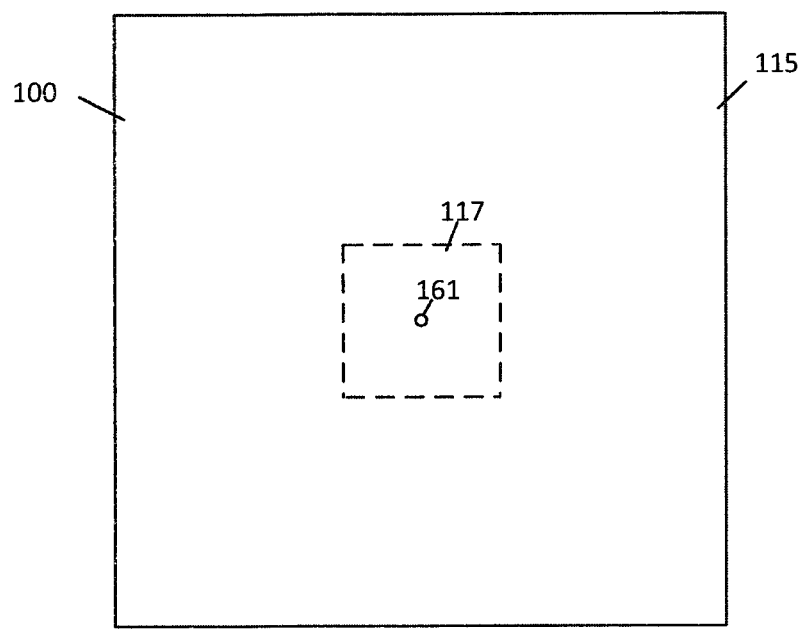
FIG. 24 illustrates a top view of a pre-drape apparatus having a needle port.

FIG. 23 illustrates a side view and FIG. 24 illustrates a top view of a two layer embodiment of a pre-drape apparatus 100. In this embodiment, the upper layer 115 can be attached over a lower layer 113 that covers an aperture 117. The upper layer 115 can include a needle port 161 which can allow a needle 163 to be inserted into the aperture 117. The needle 163 can be coupled to a syringe that can inject a sterilization solution into the aperture 117 volume. Alternatively, the needle 163 can be pressed into the skin 101 of the patient so that medication can be given to the patient. The needle port 161 can include a seal that is only opened when the needle 163 is inserted. When the needle 163 is removed, the needle port 161 is sealed to prevent fluids (liquids and gas) from entering or exiting the aperture 117 space.

In different embodiments, the aperture 117 can have different configurations. For example, the lower layer 113 can be made of a thicker material which can allow more ambient air to be above the incision zone and cause the upper layer 115 to be higher away from the skin 101 so that there is less chance of contact. In a preferred embodiment, the portion of the upper layer 115 above the incision zone skin area 107 does not have an adhesive so the upper layer 115 will not stick to the incision zone skin area 107. This area above the incision zone skin area 107 can also form a volume within which the sterilization prep solution can be held or injected. Thus, the skin 101 can form the lower surface and the upper first layer 115 can form the upper volume surface. In this embodiment, the lower layer 113 or the edges of the aperture 117 can be non-absorptive so that the lower layer 113 can hold or contain the sterilization prep solution above the incision zone skin area 107. In this embodiment, the upper layer 115 and the lower layer 113 can be made of non-absorptive materials and the lower adhesive 103 and the adhesive 105 between the upper layer 115 and the lower layer 113 can create a liquid containment volume 117. The sterilizing solution is held within the incision zone skin area 107.

In different embodiments, the sterilizing solution can be added at various times and through a nozzle on to the incision zone skin area 107 through the drape apparatus 100. The sterilizing solution can be a gel or fluid injected into the aperture region 117. A gel can have a thicker consistency which may tend to stick to the incision zone skin area 107 and may be less easily absorbed by the drape 100 material and pulled away from the incision zone. In an embodiment, a sponge or other structure can be saturated with a sterilizing solution and held in place in the aperture volume 117 above the incision zone skin area 107.

In other embodiments, a nozzle can be attached to or integrated with the upper layer 115 or the lower layer 113 to allow the sterilizing solution to flow into the volume above the incision zone. For example, the nozzle can replace the needle port 161 in the upper layer 115. The nozzle can include a valve to prevent the sterilization solution from exiting the incision zone. In an embodiment, the process can include the steps of: opening the valve, pumping the sterilizing solution into the volume above the incision zone skin area 107 and closing the valve to retain the sterilizing solution above the incision zone skin area 107. These embodiments, allow the skin area 107 to soak in the sterilizing solution from time of application until the outer drape 115 is removed.

In different embodiments, the use of the inventive multi-layer drapes can be described as part of a process that can improve efficiency and sterility in the OR. The skin of the patient can be sterilized and the multi-layer drape can be applied to the patient in a pre-surgery non sterile area of the facility (hospital). The outer surface of the upper layer can be non-sterile and all underlying layers and surfaces can be sterile. Once the patient is transferred to the OR the outer layer of drape can be removed, exposing the underlying sterile layer(s). If necessary, additional layers of drapes can be applied to the sterile layer(s). Since the patient's skin is sterilized and the drapes are applied out of the OR, the time in the OR is reduced and the cost efficiency of the surgery is improved. The sterilization time of the patient's skin is also longer which improves sterilization and reduce the chances of infection.

In other method embodiments, the outer drape layer of the multi-layer drape apparatus is removed and the aperture area in the lower drape layer is exposed. The air exposure allows the sterilizing prep solution in the aperture to dry. The surgeon can mark the skin on the incision area with marker to identify an incision line(s) and an adhesive drape can be applied to the aperture and the surgical procedure can be started.

In an embodiment, it can be desirable to allow the skin to soak for as long as possible in the prep solution to reduce the bacterial count prior to the procedure. When this soaking procedure is performed, the prep time can be extended from 3 minutes to 20-30 minutes. This technique still allows the surgeon to mark the incision site in the OR after the patient has been positioned. It reduces the draping procedure to applying a single strip of adhesive drape to a limited space in the region of the incision.

Soaking of the skin with sterilizing prep solution can be performed with a pre-drape apparatus having an aperture. In an embodiment, the inventive system can use an aperture pre-drape apparatus, which includes an aperture opening in the lower layer and an upper layer 115 that covers the lower layer and the aperture 117. In this embodiment a prep solution can be applied to the patient over the incision zone of the skin 101 and the prep solution can dry on the patient. The multi-layer pre-drape can be placed on the patient with the aperture 117 of the lower layer aligned over the incision zone. In an embodiment, the adhesive on the lower surface of the lower layer 113 can be covered with a release paper. The release paper can be removed to expose the adhesive and the multi-layer pre-drape 100 is applied to the patient with the aperture 117 over the incision zone. In this embodiment, the upper surface of the upper layer 115 is non-sterile and exposed to ambient air outside the OR while all other surfaces of the multi-layer drape 100 are sterile including the adhesive on the lower surface of the lower layer 113 and the adhesive on the interface between the upper layer 115 and lower layer 113. In an embodiment, the aperture 117 may hold the sterilization solution, which can be in the form of a gel, held within a sponge or other fluid containing structure placed in the aperture 117, a porous receptacle, or any other fluid absorbing structure that will keep the fluid in contact with the incision zone of the skin 101.

Figure 25:
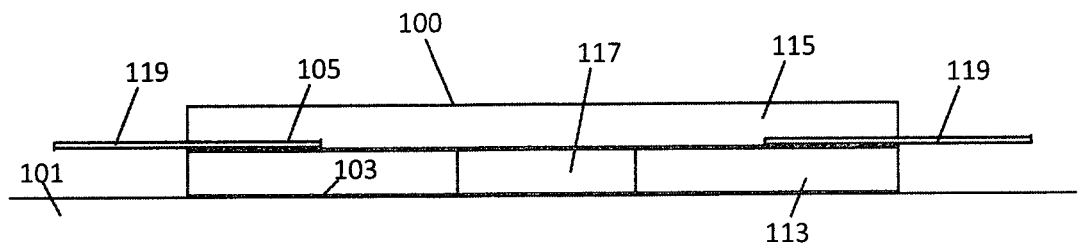
FIG. 25 illustrates a side view of a two layer embodiment of a pre-drape apparatus with a boundary material.
Figure 26:
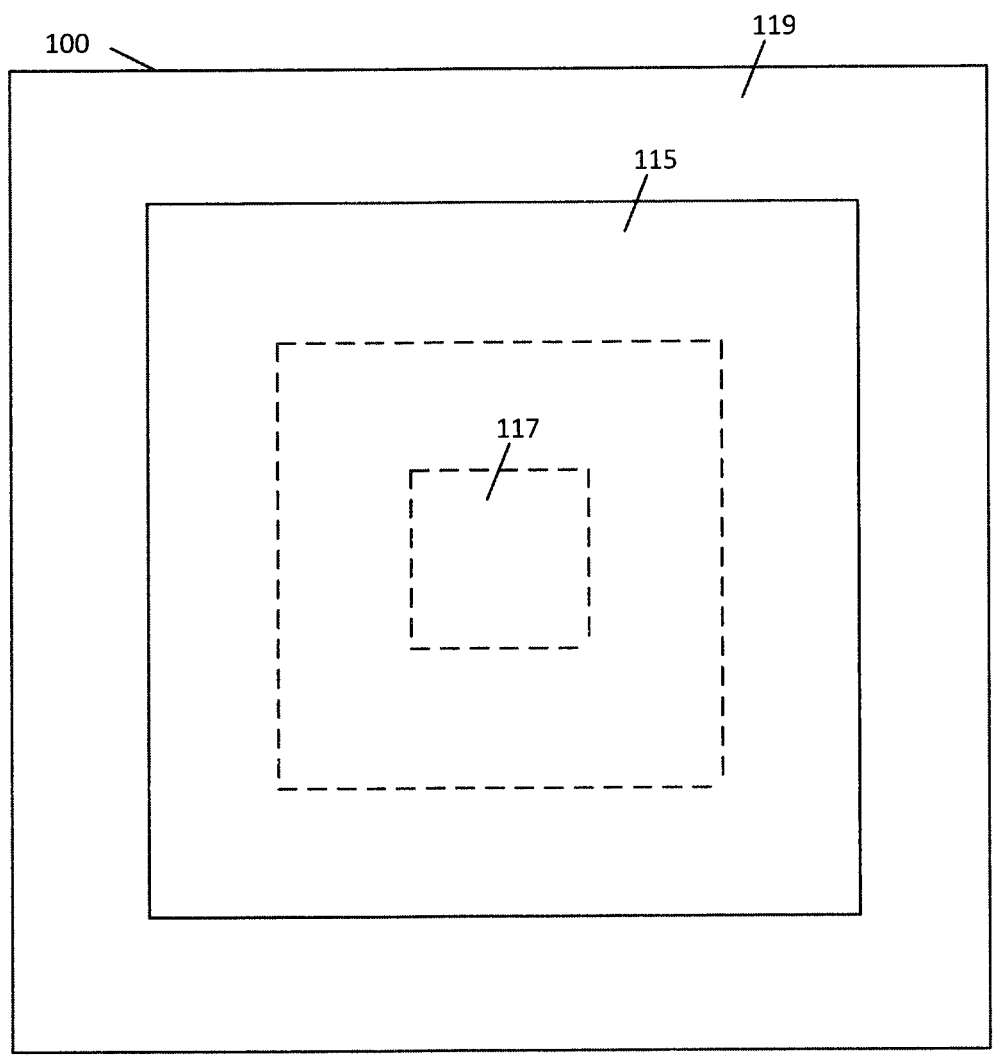
FIG. 26 illustrates a top view of a two layer embodiment of a pre-drape apparatus with a boundary material.

FIG. 25 illustrates a side view and FIG. 26 illustrates a top view of an embodiment of a multi-layered pre-drape apparatus 100 that can include a "boundary material" 119 between upper layer 115 and the lower layer 113. In the illustrated example, the boundary material 119 can be a stronger material with a thin thickness such as a sheet of plastic material that is adhesively bonded to the lower drape layer 113. The boundary material 119 can have a shape that matches the outer perimeter of the upper layer 115 and the lower layer 113. The boundary material 119 also has an inner opening that is larger than the aperture 117 in the lower drape layer 113. The multi-layer pre-drape apparatus 100 can be applied to the incision zone of the patient as described above. When the upper layer 115 is pulled off, the underlying drape 113 is exposed and the boundary material 119 can be expanded outward. In another embodiment, the lower surface of the upper layer 115 is sterile. The upper layer 115 can be cut over the aperture and folded over the boundary material 119 and/or the underlying drape 113 (in a 2 layer construction) to function as an additional drape with the sterile underside now facing up. The surgeon can then apply additional drapes to the boundary material 119 that can expand further across the patient than the multi-layered pre-drape 100. The additional drapes can be made of a durable material and have an adhesive edge which is secured to the boundary layer 119. In different embodiments, the additional drapes can be made of various materials such as: plastics like Tyvex, cloth or any other suitable durable protective materials.

Figure 27:
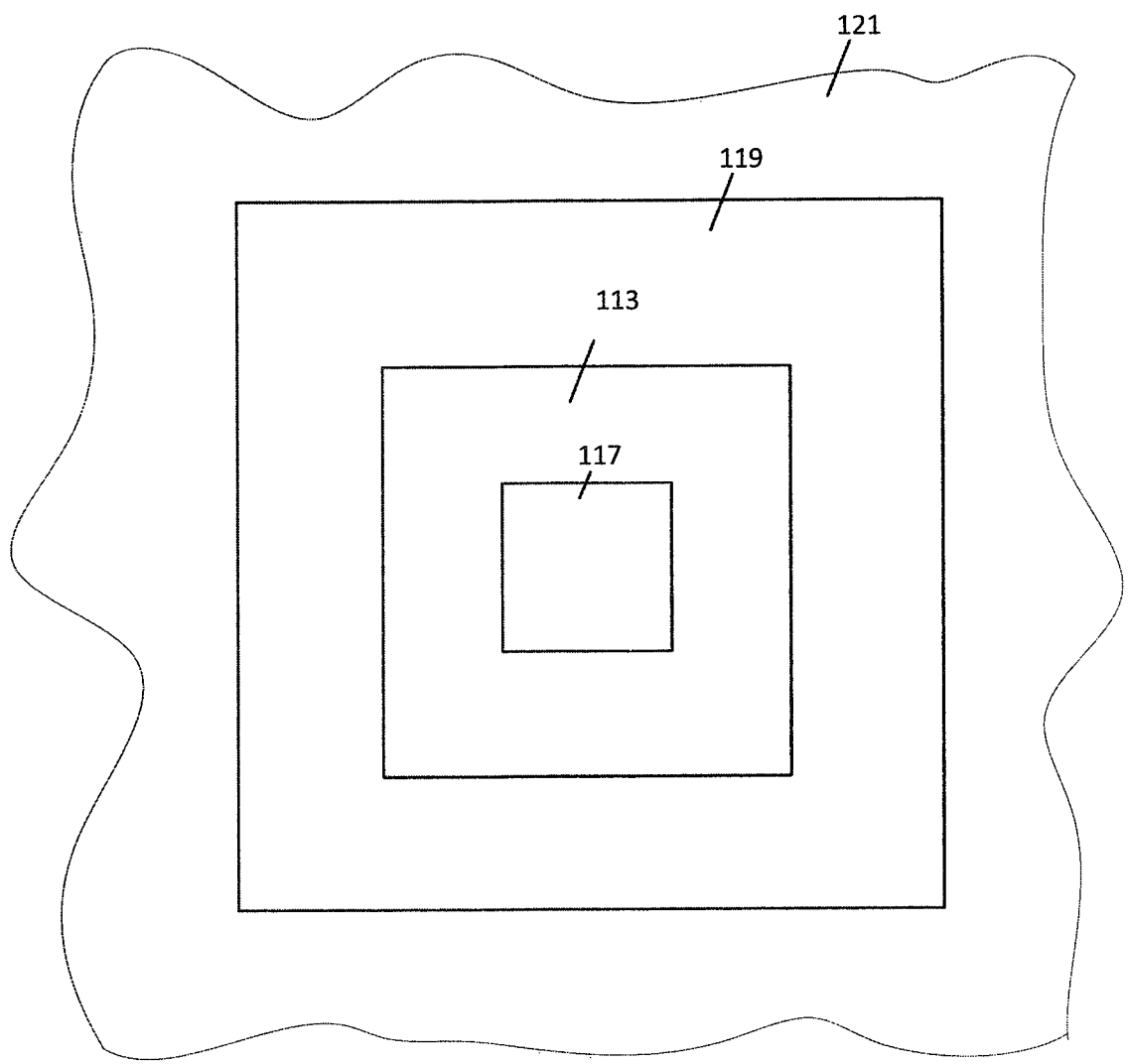
FIG. 27 illustrates a top view of a two layer embodiment of a pre-drape apparatus with a boundary material and additional drape material.

FIG. 27 illustrates a top view of an embodiment of the additional drape material 121 attached to the boundary material 119 that is attached to a lower layer 113 with an aperture 117. The additional drape 121 can include an aperture that is smaller than the perimeter of the boundary material 119. An adhesive can be applied to the edge of the boundary material 119 which can be used to secure the additional drape 121 to the boundary material 119. The adhesive can create a fluid tight seal, which prevents fluids from flowing from the upper surface of the boundary material 119 through the interface with the additional drape 121.

Figure 28:
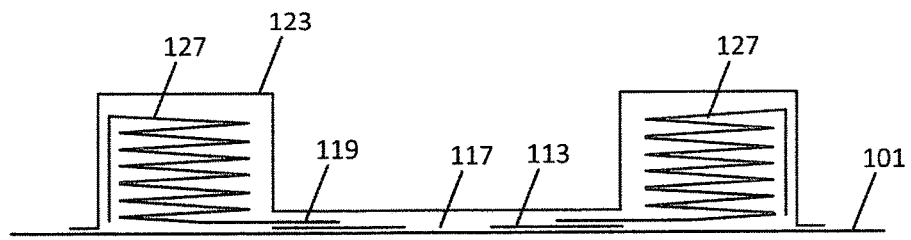
FIG. 28 illustrates a cross section side view of a multi-layer embodiment of a pre-drape apparatus with additional folded drapes.
Figure 29:
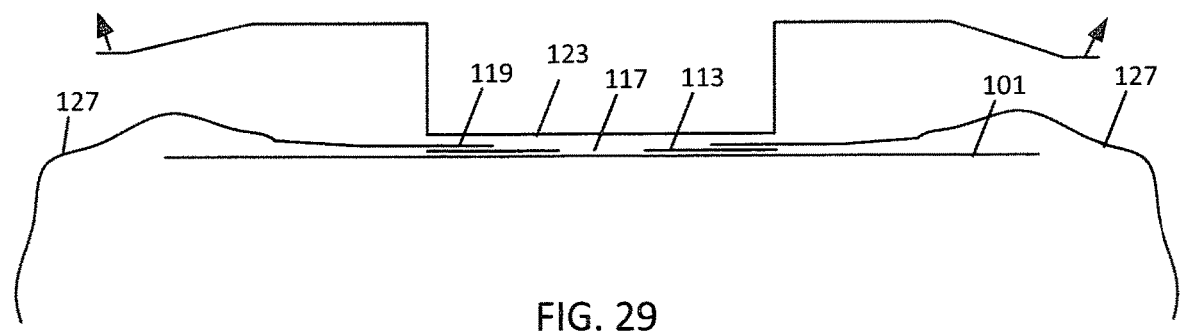
FIG. 29 illustrates a cross section side view of a multi-layer embodiment of a pre-drape apparatus with folded drapes deployed.
Figure 30:
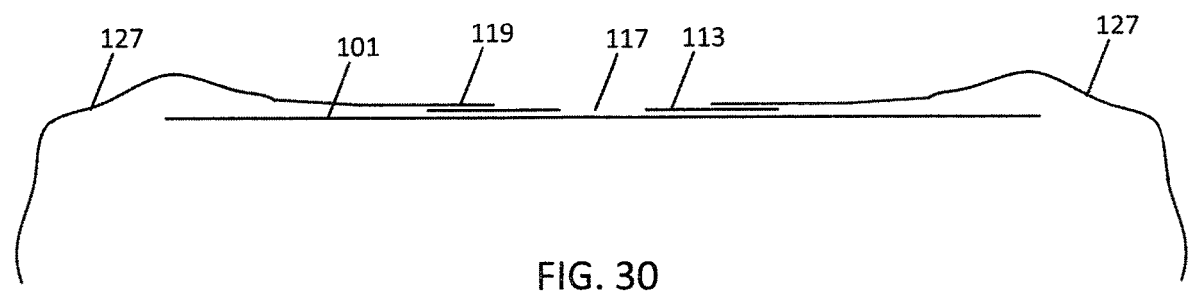
FIG. 30 illustrates a cross section side view of a multi-layer embodiment of a pre-drape apparatus with folded drapes deployed.

In some embodiments, the additional drapes can be integrated into the multi-layer pre-drape apparatus. FIG. 28 illustrates a cross sectional view of a three-layer embodiment of a pre-drape apparatus where the lower layer 113 is a planar structure as described above. The middle layer boundary material 119 includes a flat section that surrounds the surgical incision zone skin area or aperture 117 and is attached to the perimeter boundary material 119 that can be folded into draped sections 127 in an accordion manner. The upper layer can be a sterile cover 123 that can be flat over the middle incision zone 117 and raised over the folded draped sections 127. The upper layer 123 can function as a cover and hold the boundary material 119 and folded drape sections 127 in place. In an embodiment, the middle planar area can have an aperture opening 117 in the lower layer 113 and the boundary material 119. The upper drape 123 can cover the aperture 117. This embodiment of the multi-layer drape can be secured to the patient's skin 101 in the same manner as described above. The outer surface of the upper layer drape 123 can be non-sterile while all other lower layers and interfaces between the different layers can be sterile. With reference to FIG. 29, when the perimeter of the upper layer 123 is opened, the folded sections 127 of the middle drape layer can be unfolded and expanded over the sides of the patient. With reference to FIG. 30, when the folded sections 127 have been fully expanded, the center portion of the upper layer 123 can be removed to expose the aperture 117. The described process can simplify and speed the preparation of the patient prior to the surgical incision.

Figure 31:
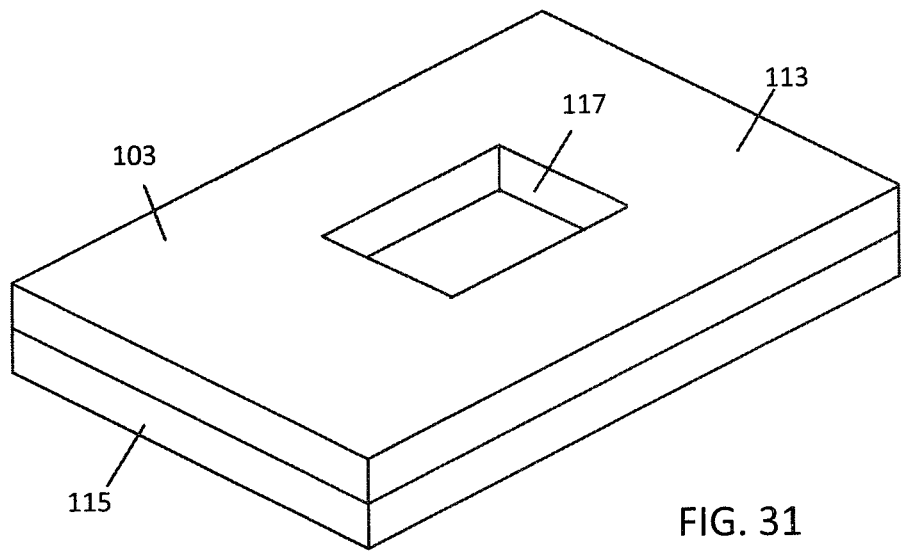
FIG. 31 illustrates a bottom perspective view of an embodiment of the multi-layered pre-drape apparatus.
Figure 32:
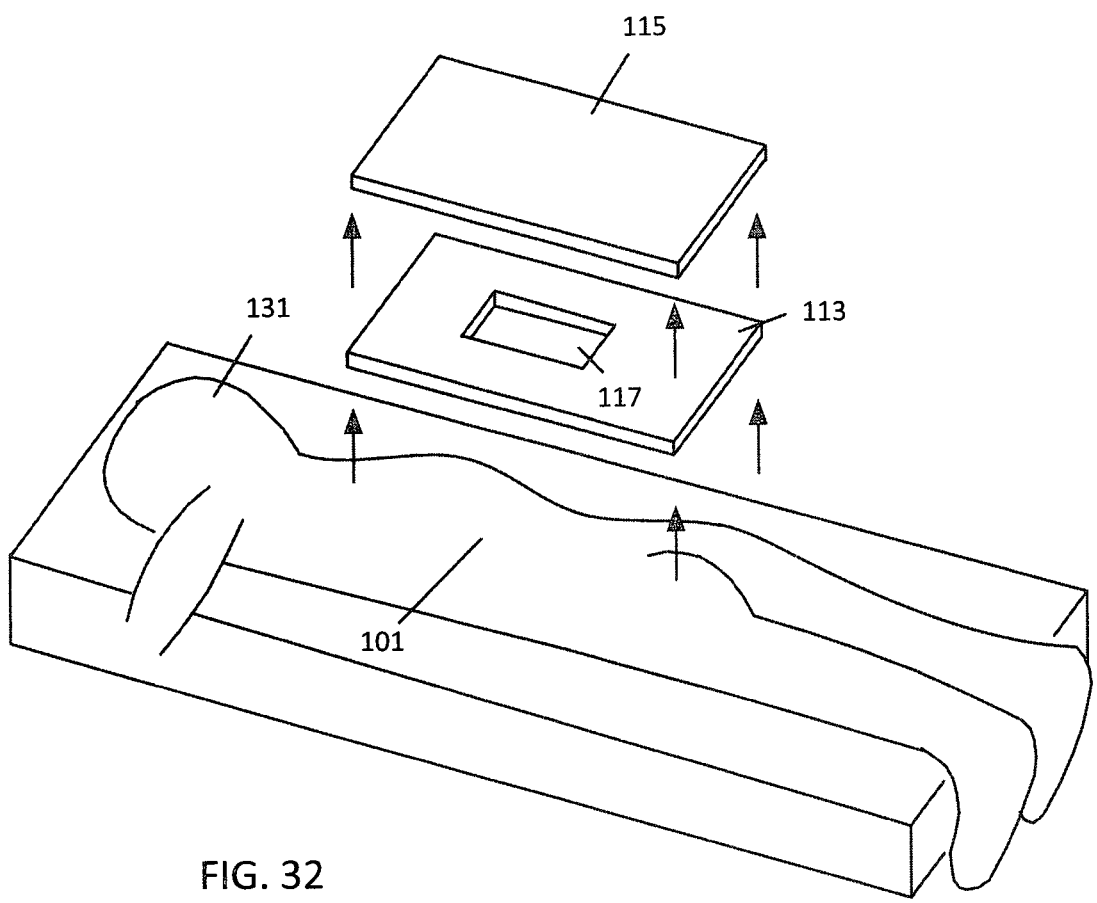
FIG. 32 illustrates a top exploded view of an embodiment of the multi-layered pre-drape apparatus on a patient.

With reference to FIG. 31, a bottom perspective view of an embodiment of the multi-layered pre-drape apparatus is illustrated. The bottom of the lower layer 113 having an adhesive surface 103 is illustrated which is attached to the skin of the patient. The middle portion of the lower layer 113 includes an aperture 117 which can hold a sterilizing prep solution. The outer surface of the lower layer is sterile and attached to an upper layer 115. With reference to FIG. 32, an illustration of how the multi-layered pre-drape can be attached to a patient 131 is illustrated. As discussed, the lower layer 113 with an aperture 117 can be attached to the skin 101 of the patient 131, in this example the back of a patient 131. The aperture 117 of the lower layer 113 can be over the incision zone. The upper surface of the lower layer 113 can be covered with an upper layer 115. The upper surface of the upper layer 115 can be non-sterile while the lower layer 113 and interfaces are sterile. The skin 101 of the patient 131 can be sterilized as described and the multi-layered pre-drape can be secured to the patient 131 outside the OR. When the patient 131 is moved into the OR, the upper layer 115 can be removed to expose the sterilized lower layer 115 and incision zone of the patient 131.

FIG. 33 illustrates a side view of an embodiment of a multi-layer pre-drape apparatus that includes an expandable tent mechanism 165 that is in a compressed configuration. The lower layer 113 can be attached to the upper layer 115 and the tent mechanism 165 can be coupled over the aperture 117 that can extend through both the upper layer 115 and the lower layer 113. The tent mechanism 165 can be transparent so that the surgical area of the skin 101 is visible.

FIG. 34 illustrates a side view of an embodiment of a multi-layer pre-drape apparatus that includes an expandable tent mechanism 165 that is in an expanded configuration. In this embodiment, the tent mechanism 165 can include an accordion type of expansion walls that has been pulled up away from the skin 101. This creates a larger volume over the aperture 117 which can be used to perform tasks on the surgical area prior to moving the patient to the OR. In an embodiment, a mechanism 166 such as a pole or support can be used to hold the tent mechanism 165 in the expanded configuration.

FIG. 35 illustrates a side view and FIG. 36 illustrates a top view of an embodiment of a multi-layer pre-drape apparatus that includes an expandable tent mechanism 165 that is in an expanded configuration that includes additional features. In this example, the tent mechanism 165 can include a shelf 170 for storing tools such as sponges and sterilization solutions. The tent mechanism 165 can include grip inserts 167 which can be used to grip a tool 169. In the illustrated example, the tool 169 can be a sponge that can be saturated with a sterilization solution. The tool 169 can have a handle that can be controlled by users through the grip inserts 167 to scrub and sterilize the skin 101 in the aperture 117. When the scrubbing is complete, the tool 169 can be placed on the shelf 170 so that the skin can dry. In an embodiment, the tent mechanism 165 can be coupled to a ventilation system that can circulate air to dry the skin 101.

Figure 37:
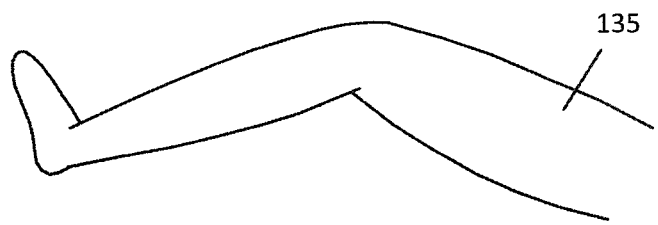
FIG. 37 illustrates a side view of a leg of a patient.
Figure 38:
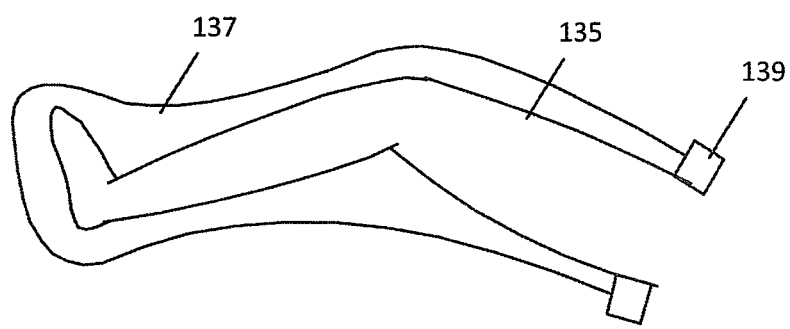
FIG. 38 illustrates a side view of leg placed in an embodiment of a prep extremity bag.

In other embodiments, a prep bag can be used to sterilize a limb of a patient. FIG. 37 illustrates a leg 135 of a patient and FIG. 38 illustrates a leg 135 that is placed in a prep extremity bag 137 where it can be sterilized prior to a surgical procedure. The inventive system utilizes various prepping technologies. In an embodiment, the components of the present invention can be contained within the prep extremity bag 137. A circular seal 139 can be placed around the circumference of the leg 135 above the knee to seal the contents within the prep extremity bag 137 to maintain sterility. The prep extremity bag 137 can be an elongated closed end tubular structure that includes a seal at an open end of the bag. The bag 137 can be pulled onto the leg 135 or limb or alternatively, the bag 137 can be rolled onto the leg 135 or limb.

Figure 39:
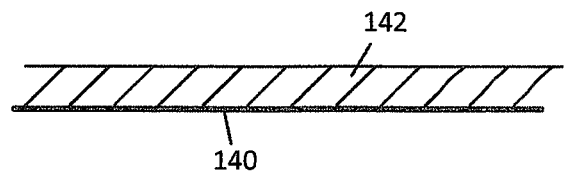
FIG. 39 illustrates a cross section view of a portion of an embodiment of a prep extremity bag.

In different embodiments, these extremity bags can contain various combinations of components such as at least one of the following: sponge, inflation mechanism, air drying mechanism, and drapes with apertures. The extremity bag can include sponge integration, which can absorb and be used to scrub and sterilize the skin of the patient. With reference to FIG. 39, a side view of a portion of a prep extremity bag is illustrated that includes an outer shell material 140 which can be bonded to an inner sponge liner 142 that can line the entire inner surface of the prep extremity bag or at least a portion of the prep extremity bag. The shell material 140 can be a flexible plastic material that is impermeable to liquids including the sterilizing prep solutions. In contrast, the inner sponge liner 142 can be a porous structure that can absorb sterilizing prep solutions. A distal portion of a limb of a patient can be placed in the prep extremity bag and a seal can be secured to a proximal portion of the limb. A sterilizing prep solution can be placed within the extremity bag and the outer surface of the extremity bag can be manipulated to press the inner sponge liner against the limb so that the limb can be scrubbed with the sterilizing prep solution and sponge liner.

Figure 40:
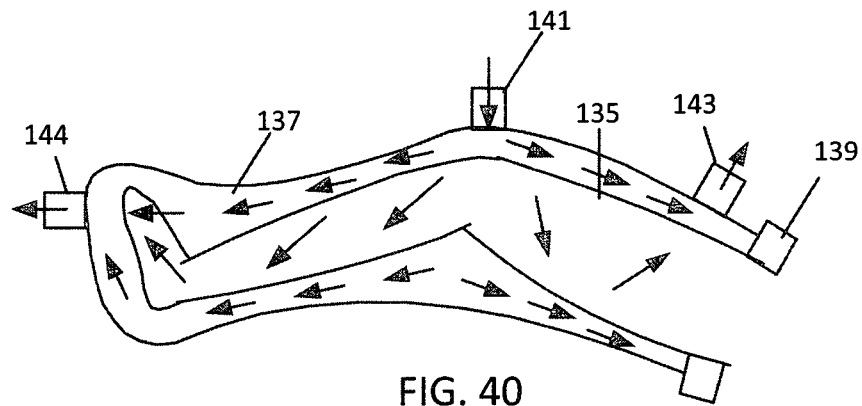
FIG. 40 illustrates a side view of leg placed in an embodiment of a prep extremity bag with a drying mechanism.

With reference to FIG. 40, the leg 135 can be dried after being sterilized with inflation technology and air drying technology. An air inlet 141 and air outlet(s) 143, 144 can be coupled to the prep extremity bag 137. The air inlet 141 can be coupled to a pump which can pump dry filtered sterile air into the extremity bag 137 which can dry the leg 135 or limb after sterilization fluid exposure. The air inlet(s) 141 and outlet(s) 143, 144 can be apertures formed in the prep extremity bag 137 to allow for air flow over the leg 135. The arrows in FIG. 40 can illustrate the air flow over the leg 135 and through the extremity bag 137. The inlet aperture can be located close to the incision area so the air flows away from the incision area. In the illustrated embodiment, the incision zone may be on the front of the patient's knee and the inlet 141 can be directly over the knee. The outlets 143, 144 can be on the opposite ends of the bag 137. In this example, there is an upper outlet 143 on a proximal portion and a lower outlet 144 on a distal portion of the bag 137. The drying air can exit through the upper outlet 143 and the lower outlet 144 can be configured to drain any residual sterilization solution from the bag 137. As long as the inlet pressure is higher than the ambient pressure outside the bag 137, the air and fluids will flow out of the outlets 143, 144 and the limb 135 will remain sterile. The leg 135 may be elevated to reduce the contact area between the leg 135 and the extremity bag 137. When the leg 135 has dried, the patient can be moved into the OR and the bag 137 or a portion of the bag 137 can be opened to expose the incision zone or the bag 137 can be opened at an aperture incision site. As discussed, the sterilization of the skin can be proportional to the exposure time to the sterilization solution. A longer exposure time to the sterilization solution will reduce the likelihood of infection. Because the exposure time is outside the OR, the cost of this sterilization process is reduced.

In an embodiment, when the bag is opened, any drapes that are integrated with the bag can be unfolded. Alternatively, the bag can be removed and sterile pre-drapes can be applied to the patient. The bag can also be combined with new sterile drapes, which can be integrated or added to the bag with an adhesive. Although the figures illustrate a leg embodiment, in other embodiments, the bag can be used with arms.

Figure 41:
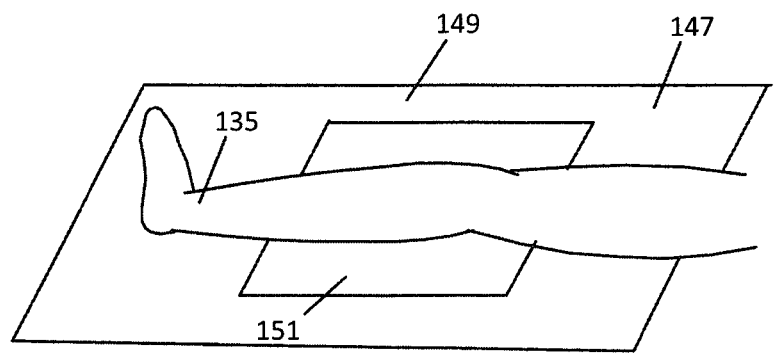
FIG. 41 illustrates a top perspective view of a leg on a sheet that forms a prep extremity bag.
Figure 42:
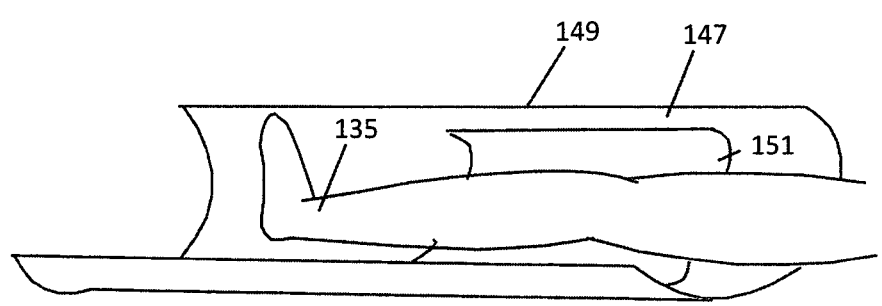
FIG. 42 illustrates a top perspective view of a leg wrapped in a sheet that forms a prep extremity bag.
Figure 43:
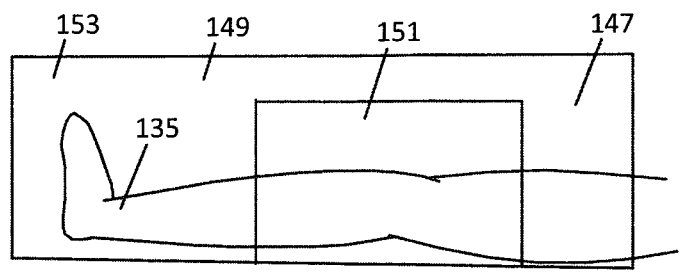
FIG. 43 illustrates a side view of a leg wrapped in a sheet that forms a prep extremity bag.

Another example of an extremity bag is illustrated with reference to FIGS. 41-48. A limb sterilization bag can be formed from a sheet 147 which is wrapped around the limb 135 and sealed. In different embodiments, the limb 135 can be cleaned with a sterile solution and can be immediately sealed in a sterile bag 147 so that the limb 135 will remain sterile before the patient is moved into the OR. With reference to FIG. 41, a leg 135 of a patient on a sheet 147 that is used to form the extremity bag is illustrated. The leg 135 can be placed with an incision zone over a non-adhesive area 151 of the sheet 147. The non-adhesive area 151 can be surrounded by an adhesive area 149. With reference to FIG. 42, the uniform thickness sheet 147 is wrapped around the leg 135 in such a way that the adhesive areas 149 of the sheet 147 are aligned with each other and the non-adhesive areas 151 can be aligned with each other. With reference to FIG. 43, a side view of the sheet 147 wrapped around the leg 135 is illustrated. The adhesive areas 149 on one side of the sheet 147 can be attached to portions of the leg 135 and the adhesive areas 149 on the opposite side of the sheet 147 above the leg 135. The non-adhesive areas 151 can surround the incision zone of the leg 135 but not adhere to the incision zone. The adhesive area 149 side surfaces of the bag can be secured to each other and sealed around the limb 135 with a contained volume. This bag sealing can be achieved through the adhesive areas 149 that are on the inner surface of the sheet material 147 that are secured to each other and the limb 135. The sheet 147 can be transparent so the user can see the limb 135 while the material is wrapped around the limb 135.

Figure 44:
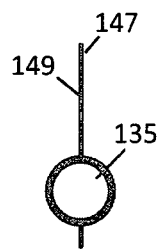
FIGS. 44-46 illustrate cross section views of leg wrapped in a sheet that forms a prep extremity bag.
Figure 45:
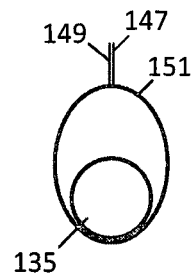
Figure 46:
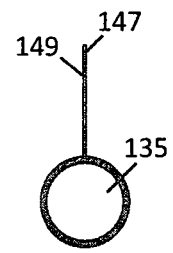

FIG. 44 illustrates a cross sectional view of a distal portion of an embodiment of the prep bag sheet 147 at the ankle portion of the leg 135. The adhesive areas 149 can form a seal with the ankle to prevent liquids from flowing out of the incision area and the bag. FIG. 45 illustrates a cross sectional view of a knee portion of the prep bag sheet 147 that can be partially inflated so that the sheet 147 is not in contact with the upper and side portions of the leg 135. In an embodiment, the non-adhesive portions 151 can include a solid flexible shell and a sponge liner, which can be saturated or impregnated with the sterilization solution. The leg can be sterilized by pressing the sponge liner against the leg so that the prep solution sterilizes the skin. FIG. 46 illustrates a cross sectional view of a distal portion of an embodiment of the prep bag sheet 147 at the thigh portion of the leg 135.

The described prep sterilization bags can used to sterilize limbs using various different methods. In the first embodiment, the bag can be secured around the limb of the patient. The open end of the bag can be sealed around the limb and the sterilization solution can be injected into the bag. The limb can then be scrubbed with the sponge on the inner surface of the bag and then the patient can be moved into the OR and the bag can be removed allowing the limb to then air dry in a sterile OR environment.

In another embodiment, the bag can be secured around the limb of the patient and the open end of the bag can be sealed around the limb. The sterilization solution can be injected into the bag and the limb can then be scrubbed with the sponge on the inner surface of the bag. An air hose which supplied clean sterile air can be coupled to the bag and the sterile air can be pumped through the bag. The air can absorb the sterilization solution, which can dry on the limb within the sterile bag. The patient can then be moved into the OR and the bag can be removed to expose the dry and sterile limb.

In another embodiment, a sterilization solution can be injected into the bag and a sponge can be sealed within the bag with the limb. The limb can be scrubbed with the sponge and sterilization solution. The patient can be moved into the OR and the bag can be opened so to allow the limb to dry in the OR. Alternatively, inputs and outputs can be coupled to the bag and the limb can be dried in the bag as described above.

In some embodiments as shown in FIG. 43, the inner surface of the prep bag can have non-uniform adhesive surfaces 151. The areas of the sheet that are adjacent to the surgical incision zone can be free of adhesives so that the adhesive will not stick to the limb 135 at the surgical site. The areas of the bag 153 surrounding the incision zone of the limb 135 can be covered with an adhesive so that when the bag 153 sticks to the limb 135 and forms a liquid seal with the bag 153. The locations of the adhesives 149 can be marked so that the bag 153 can be more accurately positioned on the patient's limb 135. The edges of the sheet 147 are sealed to each other to form a bag 153 around the limb and excess air can be removed from the bag 153. The adhesive portions of the sheet 147 can be closely attached to the limb and the non-adhesive 151 portions will not be attached to the limb. FIG. 19 illustrates a side view of a bagged leg 135 which shows the line that separates the adhesive areas 149 and the non-adhesive area 151. The upper edge of the bag 153 is sealed so that the limb 135 is sealed within the bag 153. In the illustrated embodiment, the surgical procedure is being performed on the knee where the bag 153 loosely surrounds the knee.

Figure 47:
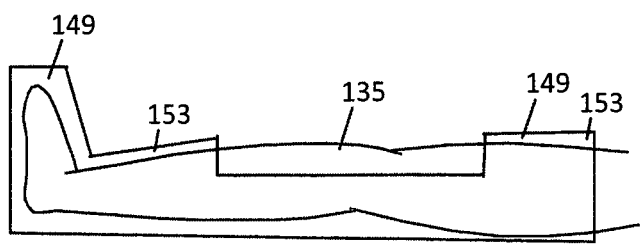
FIG. 47 illustrates a side view of a leg in a partially cut prep extremity bag.
Figure 48:
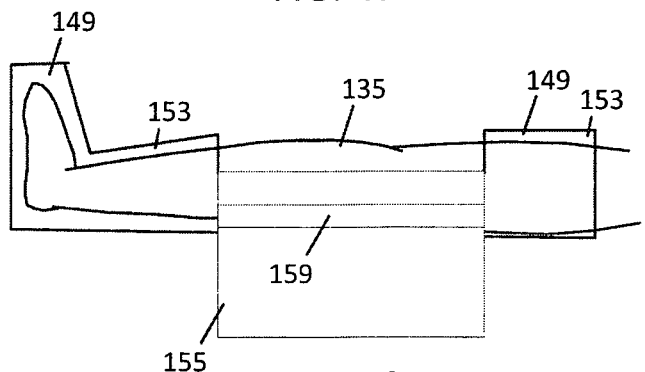
FIG. 48 illustrates a side view of a leg in a partially opened prep extremity bag with a shelf and additional drapes coupled to the prep extremity bag.
Figure 49:
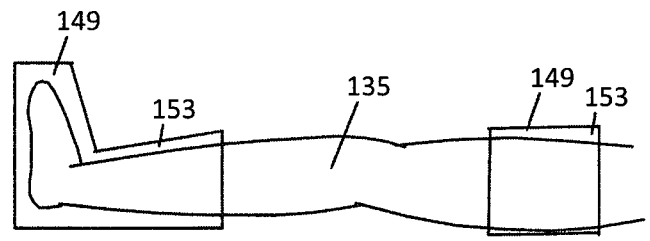
FIG. 49 illustrates a side view of a leg in a partially removed prep extremity bag.

With reference to FIG. 47, the patient can be moved into the OR and the knee portion of the bag 153 has been completely removed to expose the knee of the leg 135 for the surgical procedure. With reference to FIG. 48, a portion of the bag 153 above the front of the knee has been opened to expose the limb. The bag 153 may have features which are exposed when the bag 153 is opened. For example, in the illustrated embodiment, a shelf 159 has been built into the bag 153 that is usable when the bag 153 is opened. The shelf 159 can be used to temporarily place objects during surgery. Additional drapes 155 can be adhesively attached to the bag 153 so that the surgical procedure can be performed on the knee. In other embodiments, it may be desirable to remove all materials from the incision zone of the limb 135. With reference to FIG. 49, the patient can be moved into the OR and the knee portion of the bag 153 can then be completely removed from the entire perimeter of the knee area of the leg 135 for the surgical procedure.

Figure 50:
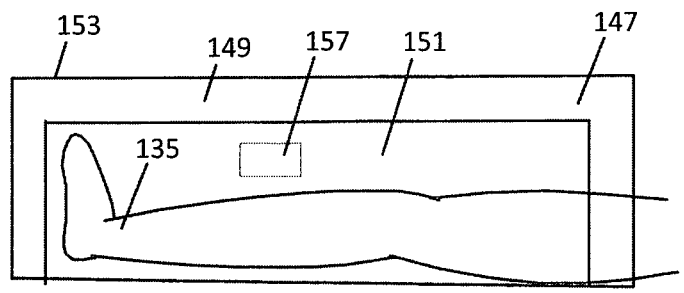
FIG. 50 illustrates a side view of a leg in a sealed prep extremity bag.

In other embodiments the sheet 147 is wrapped around the limb and only the edges of the sheet 147 are secured to each other and the upper end of the bag is secured to the upper portion of the leg as shown in FIG. 50. Most of the leg 135 can be within the non-adhesive area 151 of the sheet 147 and surrounded by the adhesive area 149. The adhesive area 149 of the sheet 147 can be secured together and the adhesive area 149 can form a seal against a perimeter of the proximal portion of the leg 135. In an embodiment, a sponge 157 can be saturated with a sterile solution and can be placed within the bag 153 and the sponge 157 can be grasped from outside the bag 153 and scrubbed against the leg 135 to sterilize the leg 135.

Figure 51:
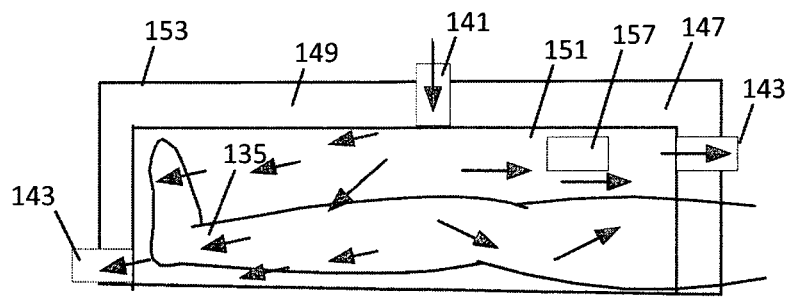
FIG. 51 illustrates a side view of a leg in a sealed prep extremity bag during drying.

With reference to FIG. 51, in an embodiment, the bag 153 can be coupled to a clean air inlet 141 and air outlets 143. The inlet 141 is positioned above the knee and the outlets 143 are by the foot and the proximal end of the bag. In an embodiment, a sponge 157 can be placed within the bag 153 and a sterilization fluid can be injected into the bag 153. The limb 135 can be cleaned and then dry sterile filtered air can flow into the bag 153 through the knee vent inlet 141 and vented out of the bag at the outlets 143 at the ends. The air flow can dry the sterilized leg 135 prior to surgery.

Again, the inner surfaces of the sheet 147 can have adhesive areas 149 and non-adhesive surfaces 151. In this example, the inner surface by the perimeter of the sheet 147 can be coated with an adhesive 149 but the area of the sheet 147 in the area of the leg 151 can not be coated with an adhesive 149 so that when the bag 153 is opened, the bag 153 will peal away without sticking to the skin of the leg 135 of the patient. In an embodiment, the bag 153 can be opened in a way that the bag itself will form part of the drape.

In different embodiments, the inventive system can be used for specific applications. In order to improve the efficiency of operations, the patient's time in the OR should be minimized. By moving surgical steps that are needed such as sterilization of an incision area of a patient outside of the OR, the efficiency can be substantially increased and the costs for surgeries can be reduced.

Figure 52:
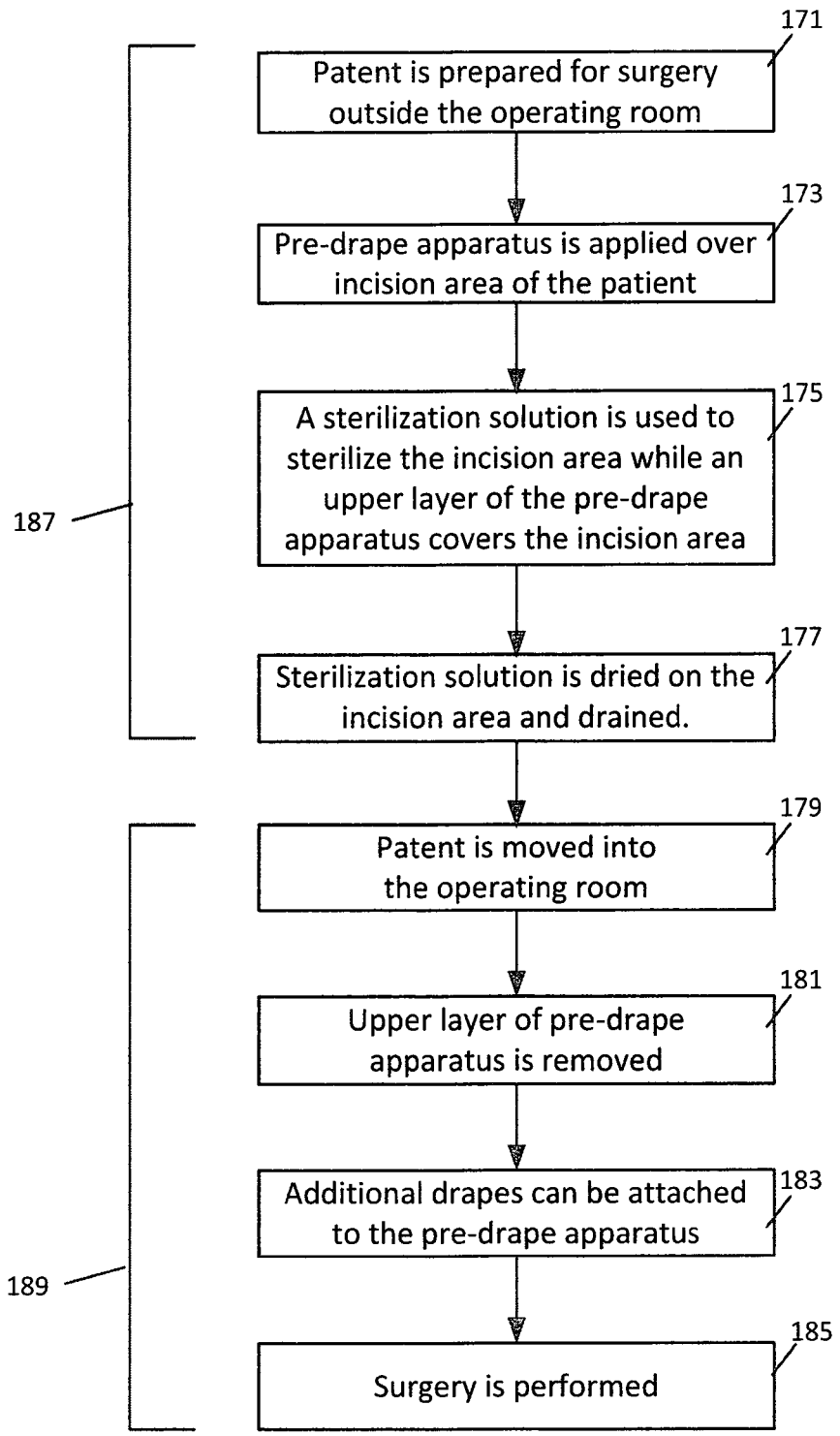
FIGS. 52-54 illustrates a flow chart of a method for using the pre-drape apparatus.

These processes can be described with reference to the flowchart illustrated in FIG. 52. The process steps can be outside of the OR 187 or inside the OR 189. For example, a patient can be prepared for surgery outside the OR 171. The pre-drape apparatus is applied over the incision area of the patient 173. In some embodiments, the pre-drape apparatus can be a planar structure that is placed on a portion of the patient's body. In other embodiments, the pre-drape apparatus can be a bag type structure that is placed around a limb of the patient. The pre-drape apparatus can have a sealing adhesive that isolates the incision area or limb from the non-sterile surroundings. A sterilization solution can be used to sterilize the incision area of the patient 175. Once the incision area in the aperture is cleaned, this area can be dried and any residual sterilization solution can be drained 177. The patient can then be moved to the OR 179. When the surgery is ready to proceed, the upper layer of the pre-drape apparatus is removed 181. Additional drapes can be attached to the pre-drape apparatus 183. Once the drapes are set up, the surgery is performed 185.

Figure 53:
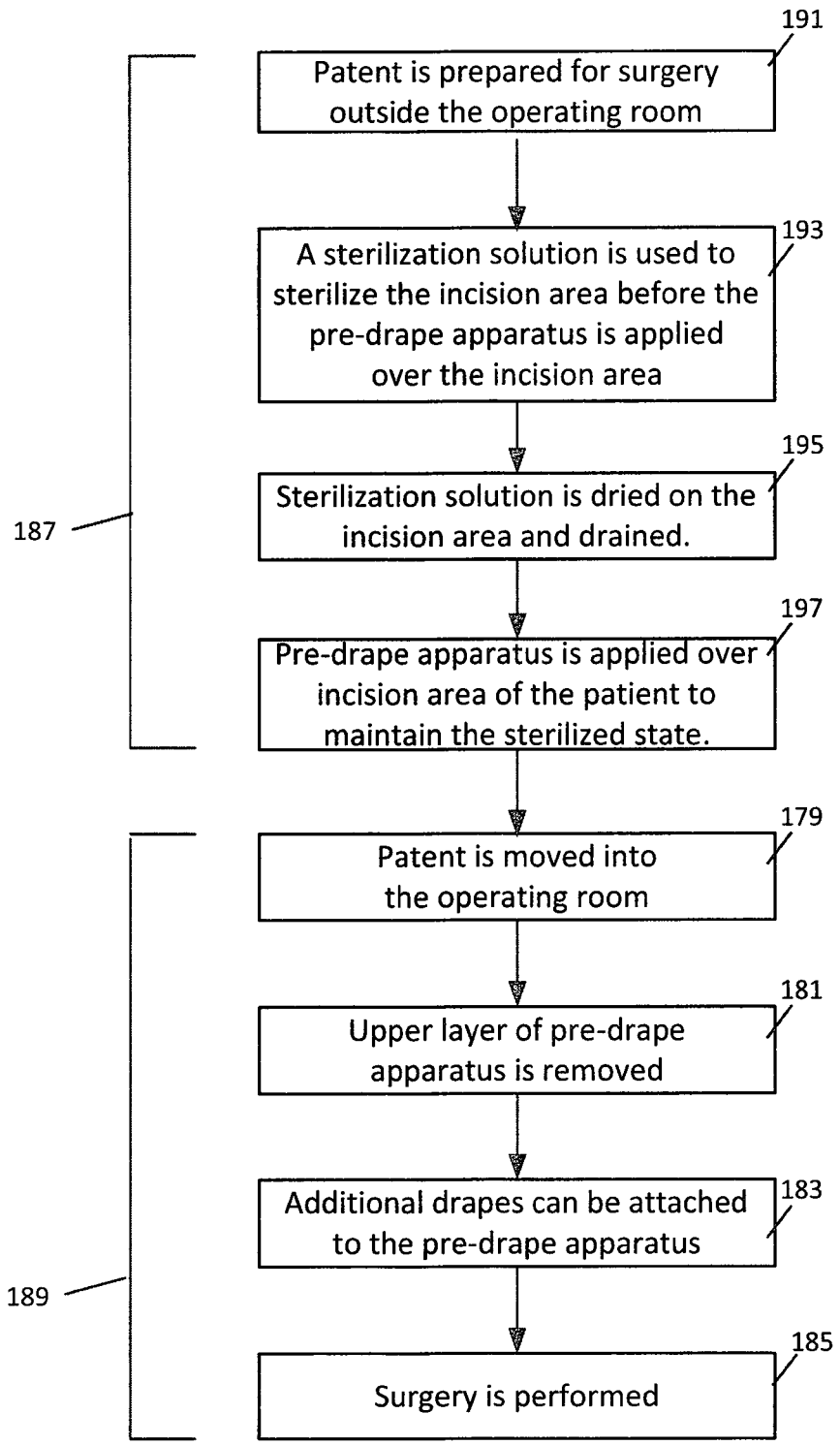

A variation on the process illustrated in FIG. 52 can be described with reference to the flowchart illustrated in FIG. 53. In this example, a patient can be prepared for surgery outside the OR 191. A sterilization solution can be used to sterilize the incision area of the patient before the pre-drape apparatus is applied. Once the incision area in the aperture is cleaned, this area can be dried 195. The pre-drape apparatus is when applied over the sterilized incision area of the patient to maintain the sterilized state 197. The patient can then be moved to the OR 179. When the surgery is ready to proceed, the upper layer of the pre-drape apparatus is removed 181. Additional drapes can be attached to the pre-drape apparatus 183. Once the drapes are set up, the surgery is performed 185.

Figure 54:
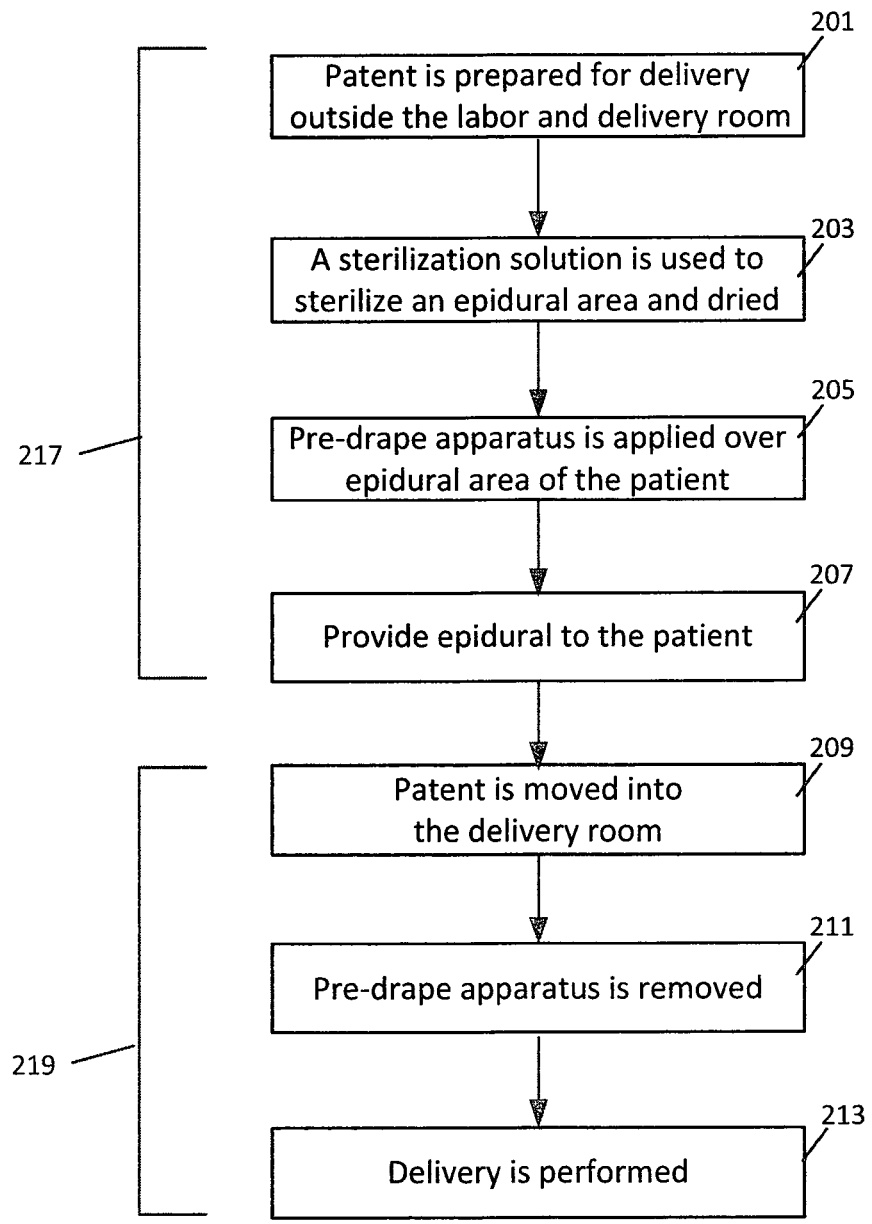

As discussed, it can be useful to perform as many procedures outside the OR as possible. These out of OR procedures can vary depending upon the needs of the patient. One example of an application is for epidurals for women who are in labor with reference to FIG. 54. Some process steps occur outside the labor and delivery room 217 while other steps occur in the labor and delivery room 219. In this application, the patient is prepared for delivery outside the labor and delivery room 201. A sterilization solution is used to sterilize an epidural area of the patient and then dried 203. The pre-drape apparatus can be applied over the epidural area of the patient 205. A topical analgesic can be applied and then the epidural can be given to the patient 207. In an embodiment, the needles for the epidural can be administered through a needle port in the upper layer of the pre-drape apparatus. If additional epidural is needed, the needle port in the pre-drape apparatus can be used again. The patient can then be moved into the labor and delivery room 209. The pre-drape apparatus can be removed 211 and the delivery can be performed 213.

Figure 55:
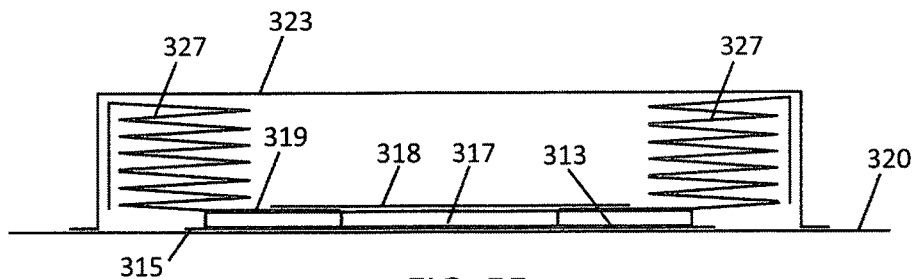
FIG. 55 illustrates a cross section side view of a multi-layer embodiment of a pre-drape apparatus with additional folded drapes in a package.

In some embodiments, the additional drapes can be integrated into the multi-layer pre-drape apparatus. FIG. 55 illustrates a cross sectional view of a pre-drape apparatus in a package that includes an outer cover 323 and a lower package layer 320. The outer surfaces of the package are non-sterile and removable so the pre-drape apparatus can be applied to the patient in the ambulatory surgical center (ASC). The skin of the patient can be sterilized. The lower package layer 320 can then be removed and the cover 323 with the pre-drape apparatus can be adhesively secured to the skin of the patient. The outer cover 323 can maintain the sterility of the area of skin covered by the pre-drape apparatus until the patient is moved into the operating room (OR).

The pre-drape apparatus includes a boundary layer 319 that is a structural material having a lower adhesive layer 313 that is attached to a release layer 315. A compressed perimeter (folded in this example) drape 327 is attached to the perimeter boundary layer 319 that can be folded in a compact accordion manner. The upper layer can be a cover 323 that covers the draped sections 327 and the boundary layer 319. The cover 323 can be attached to a lower package layer 320. The outer surfaces of the cover 323 and the lower package layer 320 can be non-sterile and functions as packaging and storable. The cover 323 and lower package layer 320 can hold the boundary material 319 and folded drape sections 327 in place prior to application to the patient. In other embodiments, the compressed drape sections can be rolled or otherwise compressed rather than being folded as illustrated.

Figure 56:
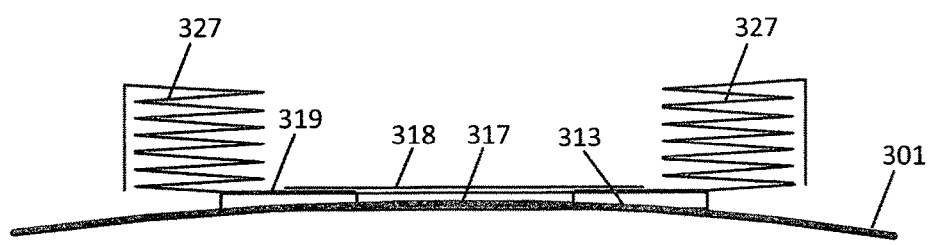
FIG. 56 illustrates a cross section side view of a multi-layer embodiment of a pre-drape apparatus with additional folded drapes.

With reference to FIG. 56, the lower package layer 320 can be removed from the cover 323 and the pre-drape apparatus. The release layer 315 can be removed from the lower adhesive layer 313 and the lower adhesive layer 313 can be attached to the sterilized skin 301 of the patient. The boundary layer 319 can include an aperture 317 that can be positioned over a surgical incision zone skin area. The aperture 317 can be covered with an aperture cover 318 which can cover the aperture 317.

Figure 57:
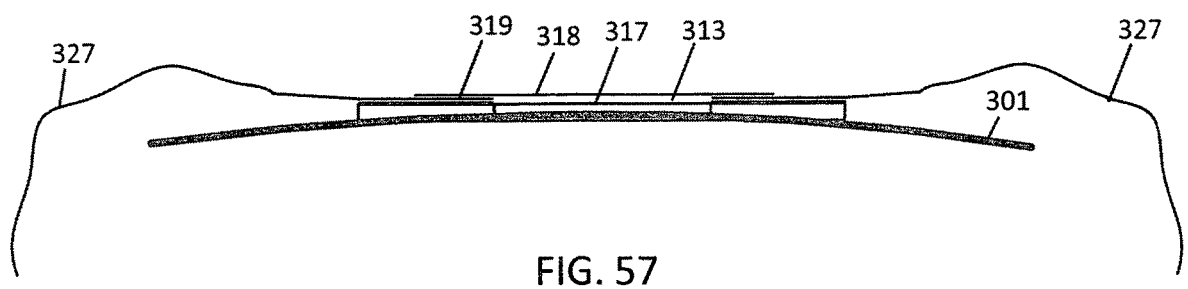
FIG. 57 illustrates a cross section side view of a multi-layer embodiment of a pre-drape apparatus with folded drapes deployed.
Figure 58:
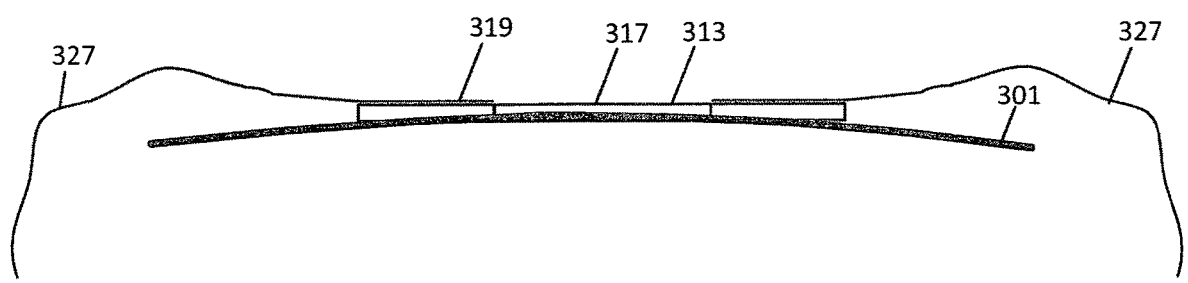
FIG. 58 illustrates a cross section side view of a multi-layer embodiment of a pre-drape apparatus with folded drapes deployed and the aperture cover removed.

In an embodiment, with reference to FIG. 57, the pre-drape apparatus can have an aperture opening 317 in the lower layer 313 and the boundary material 319. In an embodiment the multi-layer drape can be secured to the patient's skin 301 in the same manner as described above. When the upper cover 323 is opened, the folded sections 327 can be unfolded and expanded over the sides of the patient. With reference to FIG. 58, when the folded sections 327 have been fully expanded, the aperture cover 318 can be removed to expose the aperture 317. The described process can simplify and speed the preparation of the patient prior to the surgical incision.

Figure 59:
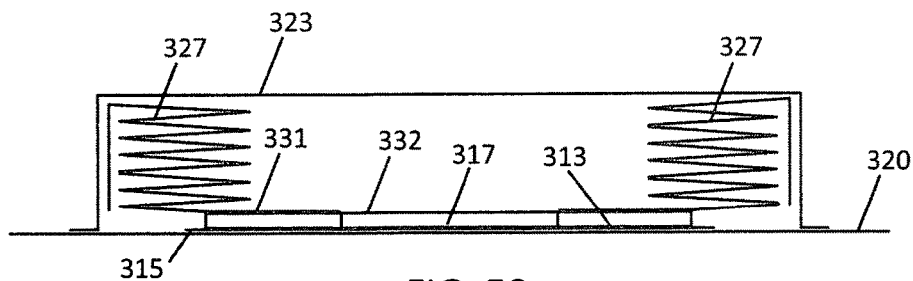
FIG. 59 illustrates a cross section side view of a multi-layer embodiment of a pre-drape apparatus with additional folded drapes in a package.

In other embodiments, the entire drape including the center and folded sections can be a unitary single piece of drape. FIG. 59 illustrates a cross sectional view of a pre-drape apparatus in a package that includes an outer cover 323 and a lower package layer 320. The outer surfaces of the package are non-sterile and removable so the pre-drape apparatus can be applied to the patient in the ambulatory surgical center (ASC). The skin of the patient can be sterilized and covered with the pre-drape apparatus. The lower package layer 320 can then be removed and the cover 323 with the pre-drape apparatus can be adhesively secured to the skin of the patient. The outer cover 323 can maintain the sterility of the area of skin covered by the pre-drape apparatus until the patient is moved into the operating room (OR).

The pre-drape apparatus includes a single piece drape that includes a boundary layer 331, an aperture portion 332 and a compressed perimeter layer. The boundary layer 331 can be coupled to a lower adhesive layer 313 and an adhesive release layer 315 can be placed over the lower adhesive layer 313. The upper layer can be a cover 323 that covers the draped sections 327 and the boundary layer 319. The cover 323 can be attached to a lower package layer 320. The outer surfaces of the cover 323 and the lower package layer 320 can be non-sterile and functions as packaging and storable. The cover 323 and lower package layer 320 can hold the boundary material 319 and folded drape sections 327 in place prior to application to the patient. In other embodiments, the compressed drape sections can be rolled or otherwise compressed rather than being folded as illustrated.

Figure 60:
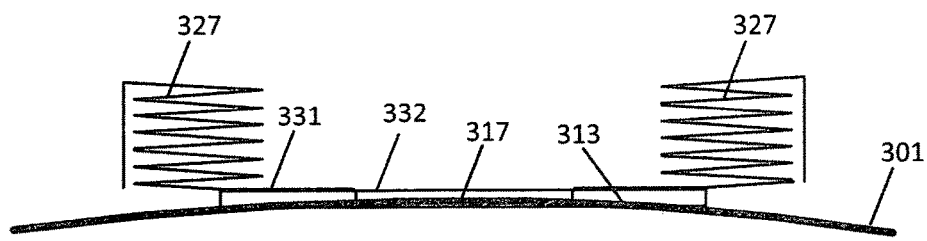
FIG. 60 illustrates a cross section side view of a multi-layer embodiment of a pre-drape apparatus with additional folded drapes.

With reference to FIG. 60, the lower package layer 320 can be removed from the cover 323 and the pre-drape apparatus. The release layer 315 can be removed from the adhesive layer 313 and the adhesive layer 313 can be attached to the sterilized skin 301 of the patient. The adhesive layer 313 can include an aperture 317 that can be positioned over a surgical incision zone skin area. The drape aperture portion 332 can cover the aperture 317 in the adhesive layer 313.

Figure 61:
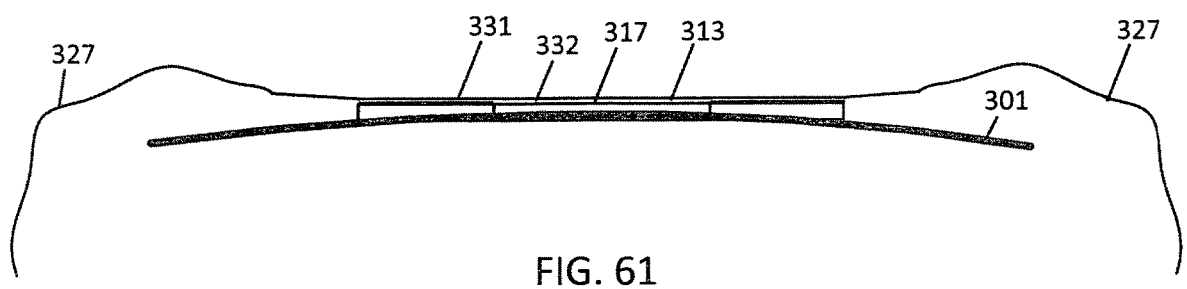
FIG. 61 illustrates a cross section side view of a multi-layer embodiment of a pre-drape apparatus with folded drapes deployed.
Figure 62:
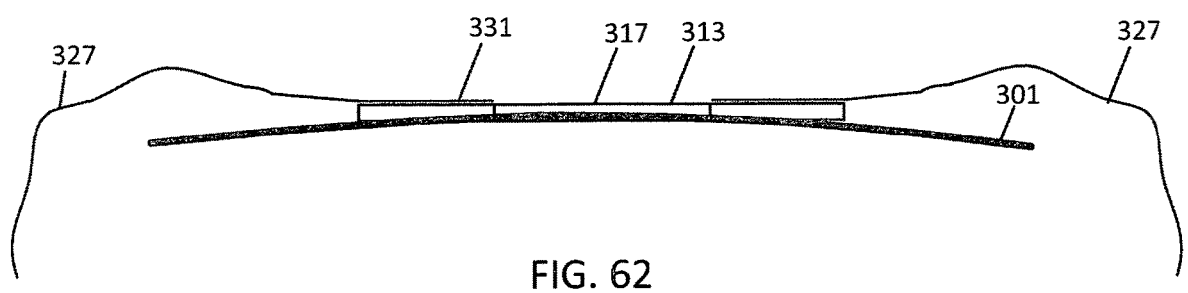
FIG. 62 illustrates a cross section side view of a multi-layer embodiment of a pre-drape apparatus with folded drapes deployed and the aperture cover removed.

In an embodiment, with reference to FIG. 61, when the upper cover 323 is opened, the folded sections 327 can be unfolded and expanded over the sides of the patient. With reference to FIG. 62, when the folded sections 327 have been fully expanded, the drape aperture portion 332 can be removed by cutting or tearing away the drape aperture portion 332 to expose the aperture 317. The described process can simplify and speed the preparation of the patient prior to the surgical incision.

Figure 63:
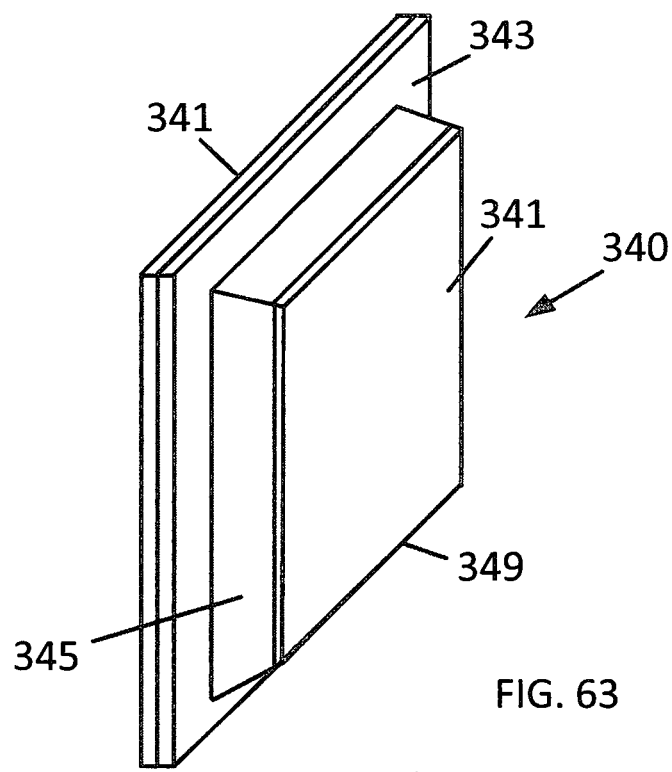
FIG. 63 illustrates a perspective view of a pre-drape apparatus in a closed configuration.
Figure 64:
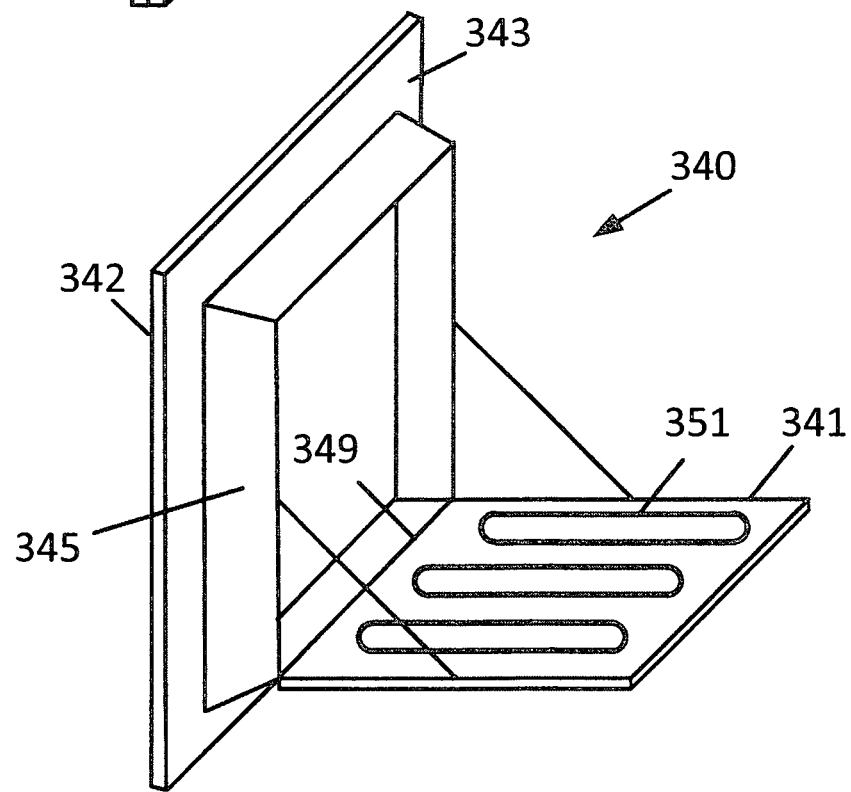
FIG. 64 illustrates a perspective view of a pre-drape apparatus in an open configuration.
Figure 65:
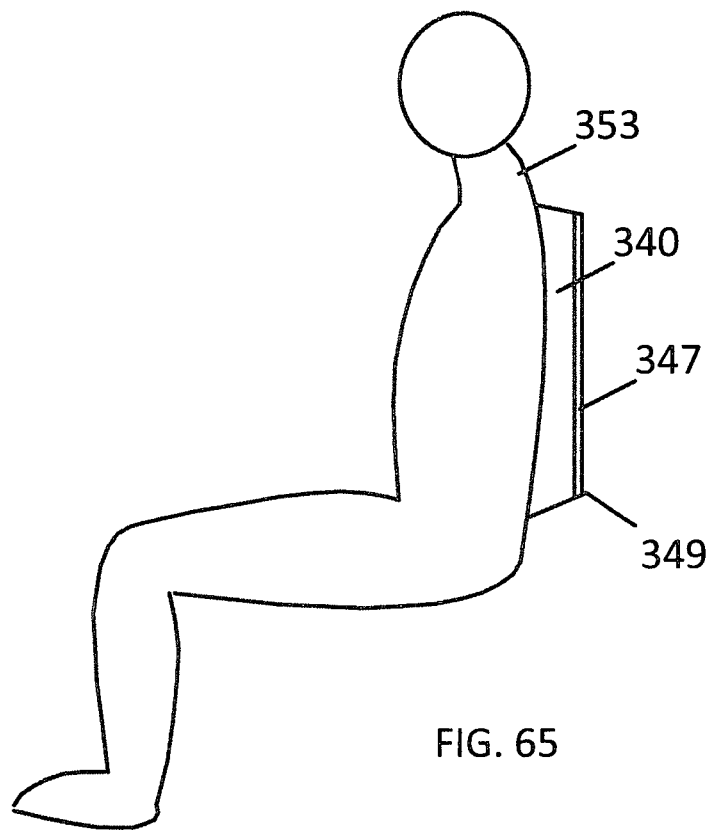
FIG. 65 illustrates a side view of a pre-drape apparatus in a closed configuration attached to a patent's back.
Figure 66:
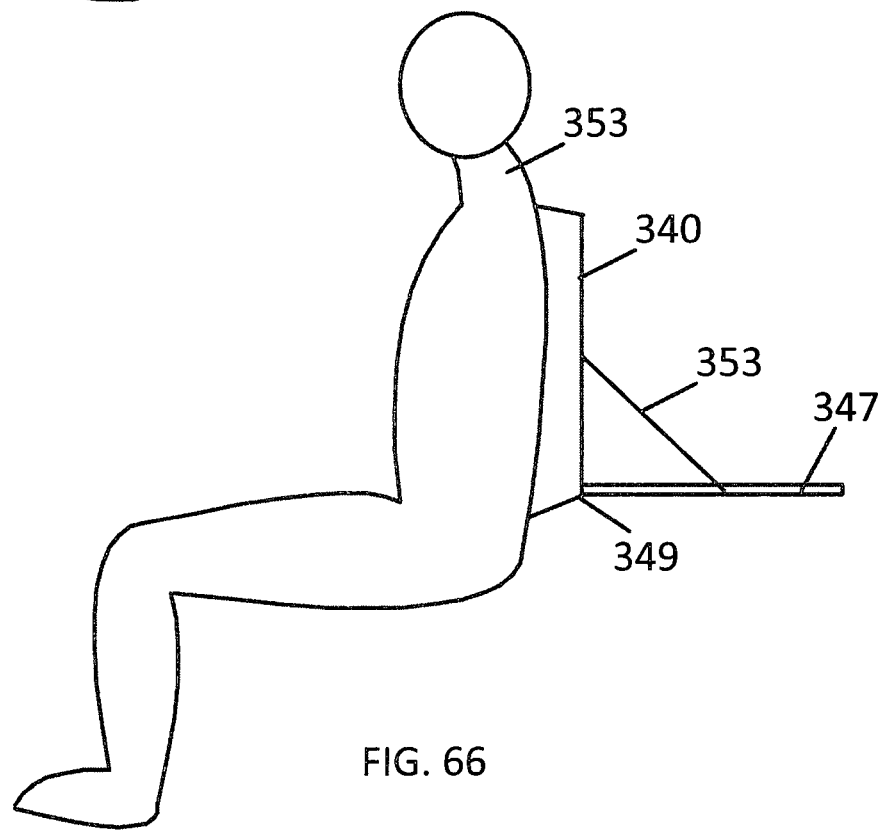
FIG. 66 illustrates a side view of a pre-drape apparatus in an open configuration attached to a patent's back.

In different embodiments, the inventive pre-drape apparatus can be a structure that is attached to a patient's torso such as the patient's back. In this embodiment, with reference to FIG. 62, the pre-drape apparatus 340 can have a raised structure that defines a volume. The pre-drape apparatus 340 can have walls 345 coupled to a door 347. The walls 345 can be coupled to an interface surface 343 that can have an adhesive 341 that can be used to secure the pre-drape apparatus to a patient. The door 347 can be coupled to a wall 345 of the pre-drape apparatus with a hinge 349. With reference to FIG. 63, the door 351 can be opened and tools 351 can be attached to the inner surface of the door 351. With reference to FIG. 64, a patient's back can be sterilized and the patient 353 can sit upright. The pre-drape apparatus 340 can be secured to the patient's back with the adhesive on the distal edge of the walls 345. The pre-drape apparatus 340 can be placed over an incision area of the patient 353 and the skin of the patient 353 covered by the pre-drape apparatus 340 can be sterilized outside the operating room. With reference to FIG. 65, the pre-drape apparatus 340 can be attached to the sterilized skin and the door 347 can be opened exposing the back skin of the patient 353. The opened door 351 can be rotated to a substantially horizontal surface. The door 351 can be supported in a horizontal position by support members 353, which can be adjustable length lines. In the opened position, the door functions as a shelf for the tools 351 such as a scalpels, syringes, a needle drivers, sutures, sponges, clamps, etc.

Figure 67:
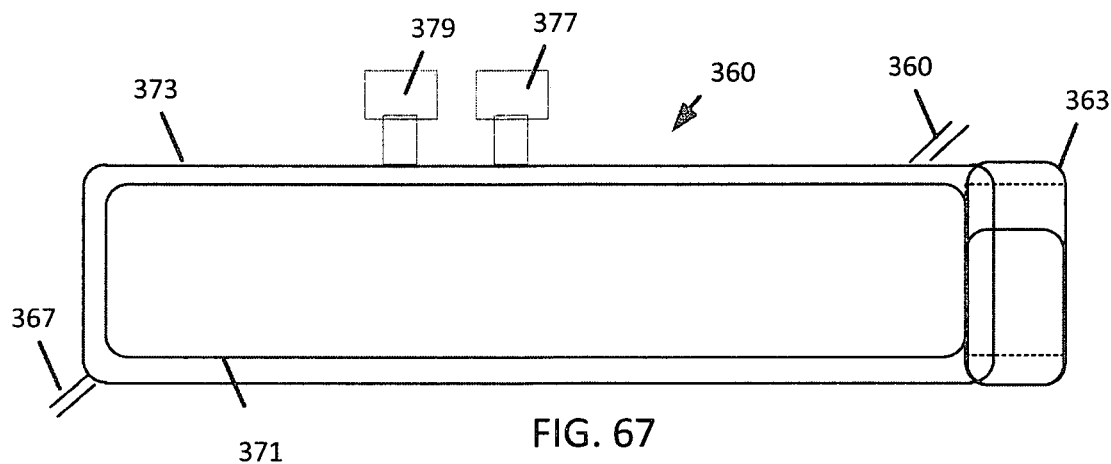
FIG. 67 illustrates a side view of an embodiment of a prep extremity bag with a tourniquet.

As discussed above with reference to FIG. 38, a prep extremity bag can be used to sterilize a limb outside the operating room prior to a surgical procedure. With reference to FIG. 67 an embodiment of a prep extremity bag 360 is illustrated that includes a bag portion 361 and a tourniquet 363. The bag portion 361 can also include an inlet 365 and an outlet 367. The bag portion 361 may also include an inner bag 371 and an outer bag 373.

Figure 68:
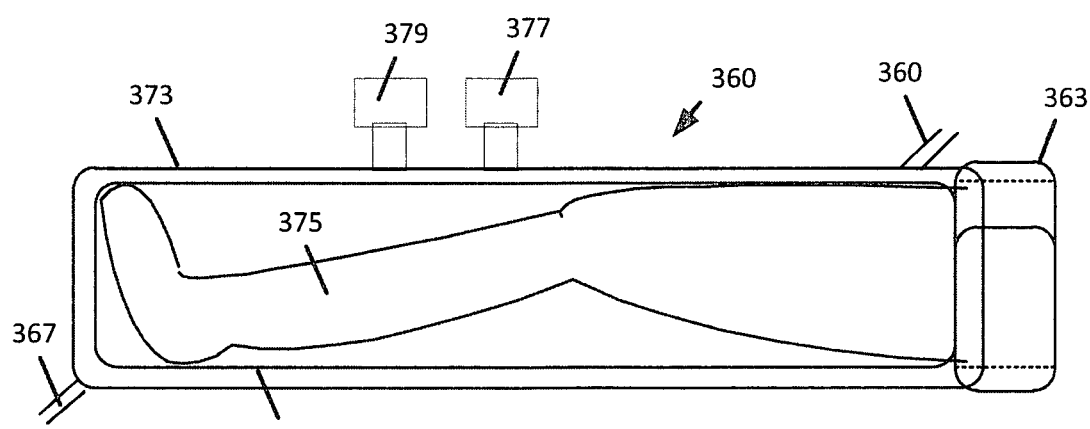
FIG. 68 illustrates a side view of an embodiment of a limb placed in a prep extremity bag with a loose tourniquet.
Figure 69:
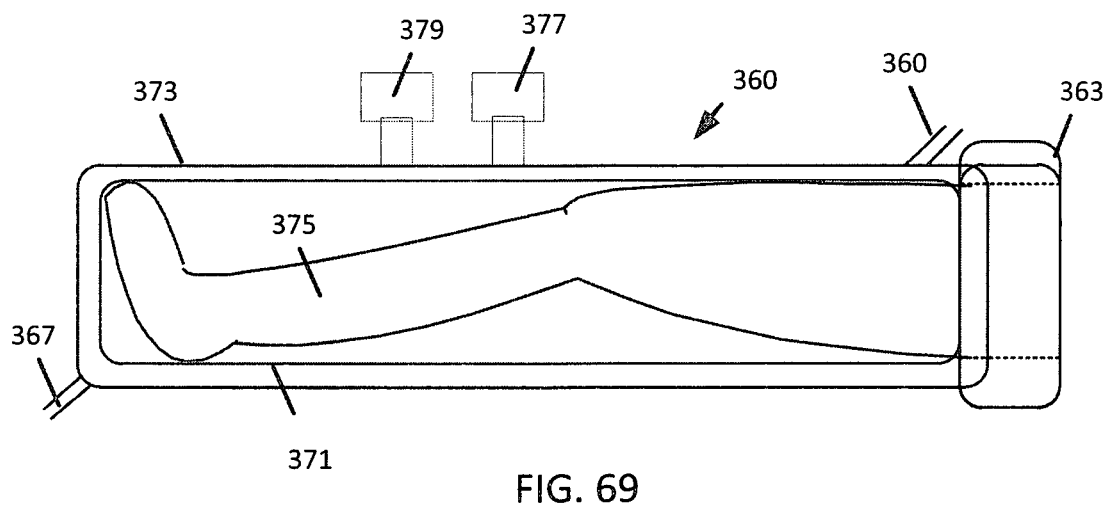
FIG. 69 illustrates a side view of an embodiment of a limb placed in a prep extremity bag with a tightened tourniquet.

With reference to FIG. 68, a leg limb 375 is placed in the prep extremity bag 360 and the inner surface of the tourniquet 363 can be sealed against the skin of the limb 375. The tourniquet 363 has not been actuated to compress the limb 375. A cleaning fluid can be injected into the prep extremity bag 360 between the limb 375 and the inner bag 371. The outer bag 373 and the inner bag 371 can create a bladder that can be inflated and pressurized through a gas inlet valve 377 coupled to a gas pressure source and then depressurized through an outlet valve 379. When the outer bag 737 is pressurized, the inner bag 371 is compressed against the limb 375. The pressurizing and depressurizing the outer bag 737 can compress the cleaning fluid against the limb 375 and circulate the cleaning fluid around the limb 375 to sterilize the limb 375. The limb cleaning can be performed with a specific volume of cleaning fluid and a specific number of pressure cycles, which can have specific pressure and pressurized/depressurized durations. When the cleaning cycle is completed, the outlet valve 367 is opened and clean air or gas can be injected through the inlet valve 365 to inflate the inner bag 371. The used cleaning fluid can settle at the bottom of the inner bag 371 and the gas pressure can force the cleaning fluid out of the inner bag 371 through the outlet valve 367. The clean gas can continue to flow through the inlet valve 365 to dry the limb 375. All of the described process steps can be performed outside the operating room. The sterilized limb 375 can now be ready for surgery in the operating room.

When the patient is moved into the operating room, the tourniquet can be actuated to compress the limb 375. The prep extremity bag 360 can be opened in the operating room to access the incision areas of the limb 375. Drapes can be attached to the prep extremity bag 360 or the prep extremity bag 360 can have integrated drapes, which can be deployed after the prep extremity bag 360 is opened.

Figure 70:
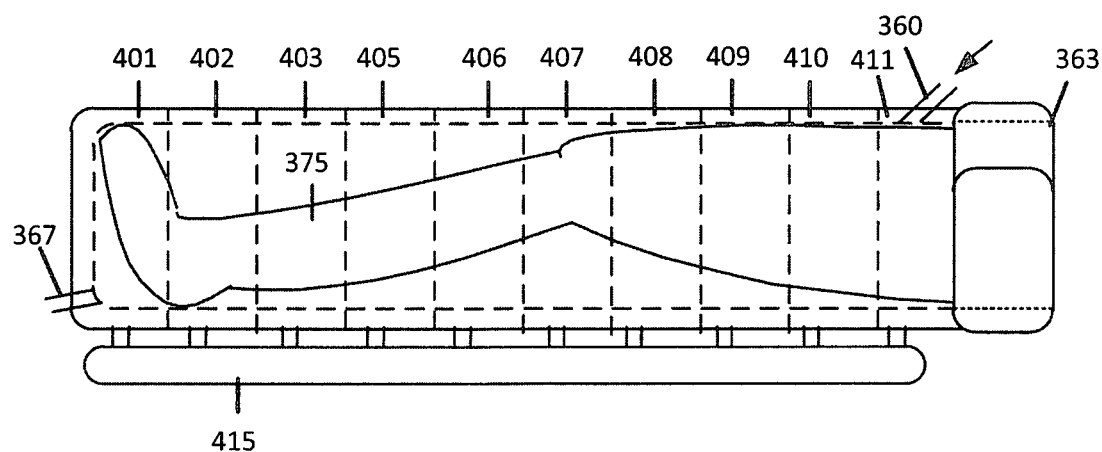
FIG. 70 illustrates a side view of an embodiment of a limb placed in a multi-bladder prep extremity bag with a tourniquet.
Figure 71:
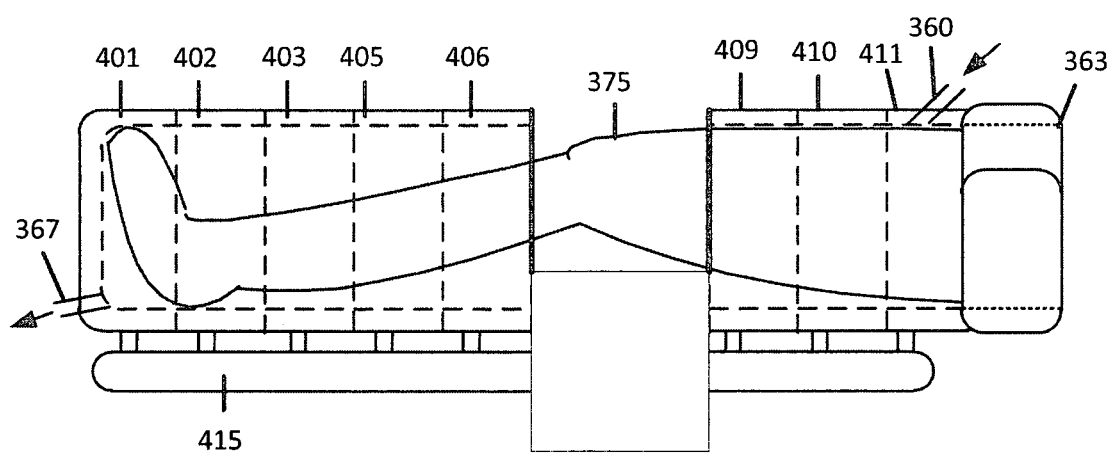
FIG. 71 illustrates a side view of an embodiment of a limb placed in a multi-bladder prep extremity bag with a portion of the bag opened.

With reference to FIG. 70, another embodiment of a prep extremity bag 360 is illustrated that includes a plurality of annular bladders 401-411 and a tourniquet 363. The annular bladders 401-411 can be attached to a gas control manifold 415, which can control the gas pressure for each of the annular bladders 401-411. The limb 375 can be placed in the prep extremity bag 360 and the inner surface of the tourniquet 363 can be sealed against the limb 375. Cleaning fluid can be injected into the prep extremity bag 360 and the gas control manifold 415 can independently control the pressure in each of the annular bladders 401-411 to control the flow of the cleaning solution around the limb 375. For example, the control manifold 415 can provide sequential pressurization of the annular bladders 401-411 to drive the cleaning fluid from one end of the limb to the other end. This cleaning fluid movement can flow over the limb 375 and cause the limb 375 to be sterilized. In an embodiment, the system can control the pressure and timing sequence patterns for each of the annular bladders 401-411 and the volume of cleaning fluid. Once the cleaning sequence is completed, the drain valve 367 can be opened and gas can be applied through the inlet valve 360. The cleaning fluid can be drained from the prep extremity bag 360 and clean gas can continue to flow into the prep extremity bag 360 to dry the limb. Once the limb is dried, the drain valve can be closed to inflate the prep extremity bag 360 which can keep the inner surfaces away from the limb to promote drying. Thus, the system provides an automated method for sterilizing the limb. With reference to FIG. 71, once the limb 375 is sterilized and dried, the patient can be moved to the operating room, the tourniquet 363 can be compressed around the limb 375 and a portion of the prep extremity bag 360 can be opened to expose the incision area of the limb 375. In this example, the portions of the prep extremity bag 360 surrounding the knee have been opened. However, in other embodiments, any other portion(s) of the prep extremity bag 360 or the prep extremity bag 360 entire can be opened.

Figure 72:
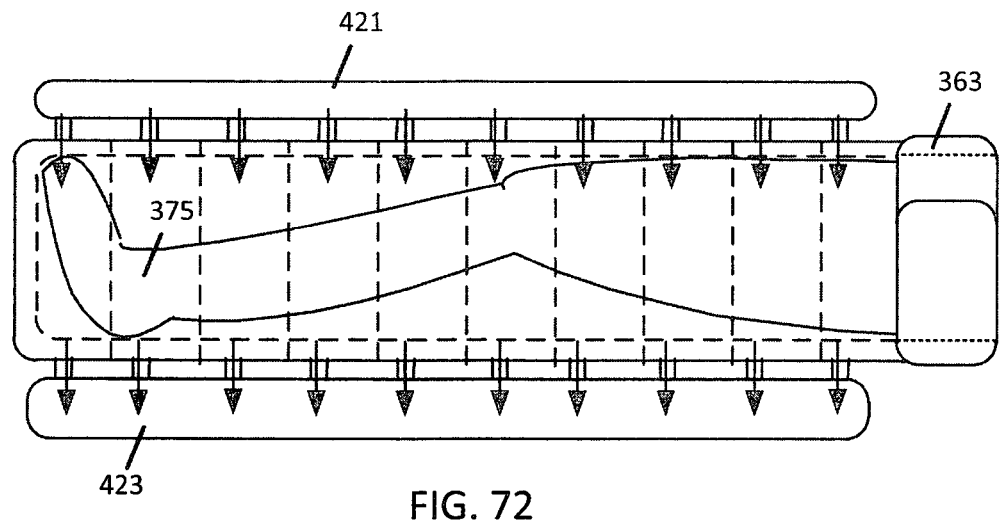
FIG. 72 illustrates a side view of an embodiment of a limb placed in a multi-bladder prep extremity bag with multiple fluid inlets and multiple fluid outlets.

With reference to FIG. 72, another embodiment of a limb sterilization system is illustrated. In this embodiment, an inlet fluid manifold 421 is coupled to a top portion of the prep extremity bag 360 and an outlet fluid manifold 423 is coupled to the bottom portion of the prep extremity bag 360. The limb 375 is placed in the prep extremity bag 360 and the tourniquet 363 is sealed against the limb 375. The inlet fluid manifold 421 can direct cleaning fluid inlet into the top portions of the prep extremity bag 360 and the cleaning solution can flow down around the limb 375 and the cleaning solution can be drained from the bottom of the prep extremity bag 360 through the outlet fluid manifold 423. In some cases, it can be beneficial to direct fluids in a specific direction across the limb 375, so it is possible for the inlet fluid manifold 421 to direct more cleaning fluid through specific inlets to the prep extremity bag 360. The cleaning solution can drain through any one of the outlets coupled to the outlet fluid manifold 423. The prep extremity bag 360 can have a plurality of annular bladders as described above with reference to FIG. 70. While the cleaning solution is flowing onto the limb 375, the bladders can be pressurized to compress the prep extremity bag 360 against the limb 375. As discussed, the pressurization of the bladders can be performed to compress the cleaning solution against the limb 375 and circulate the cleaning solution within the prep extremity bag 360. Once a specific sequence of cleaning solution injections and bladder pressurizations are performed for a designated time, the limb can be sterilized. Clean gas can be directed from the inlet fluid manifold into the prep extremity bag 360 to force the cleaning solution through the drains coupled to the outlet fluid manifold 423. Once all of the cleaning solution is removed from the prep extremity bag 360, clean gas can continue to flow into the prep extremity bag 360 to dry the limb 375.

Figure 73:
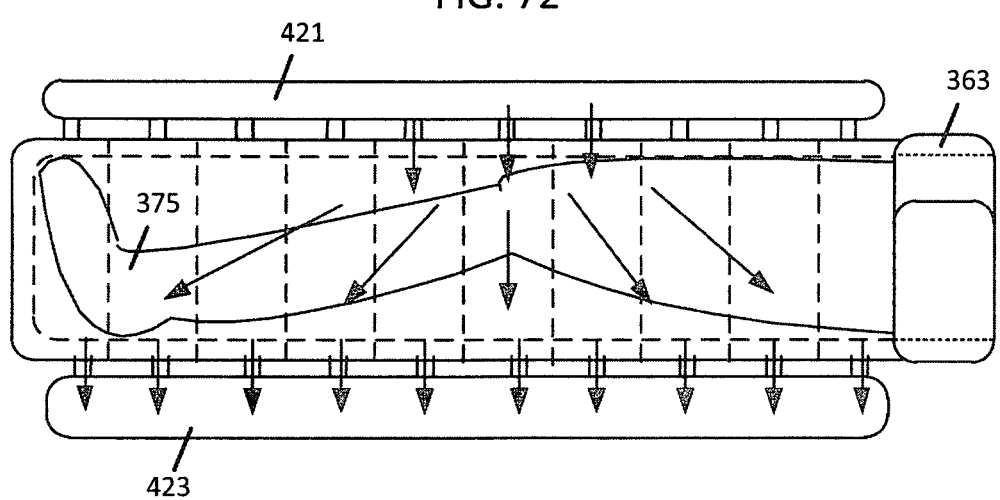
FIG. 73 illustrates a side view of an embodiment of a limb placed in a multi-bladder prep extremity bag with a fluid inlet manifold directing fluid through the center fluid inlets.

With reference to FIG. 73, in some embodiments the inlet manifold 421 can direct the clean gas through specific inlet ports into the prep extremity bag 360 from the inlet manifold 421. In the illustrated example, the clean gas can flow through the inlets directly above the knee portion of the limb and not flow into the prep extremity bag 360 from other inlet ports. This gas flow pattern can cause the sterilization fluid to flow away from the knee portion of the limb minimizing the chances that any contaminants may flow towards the knee. Residual cleaning solution and drying gases can flow into the outlets and into the outlet fluid manifold 423.

Figure 74:
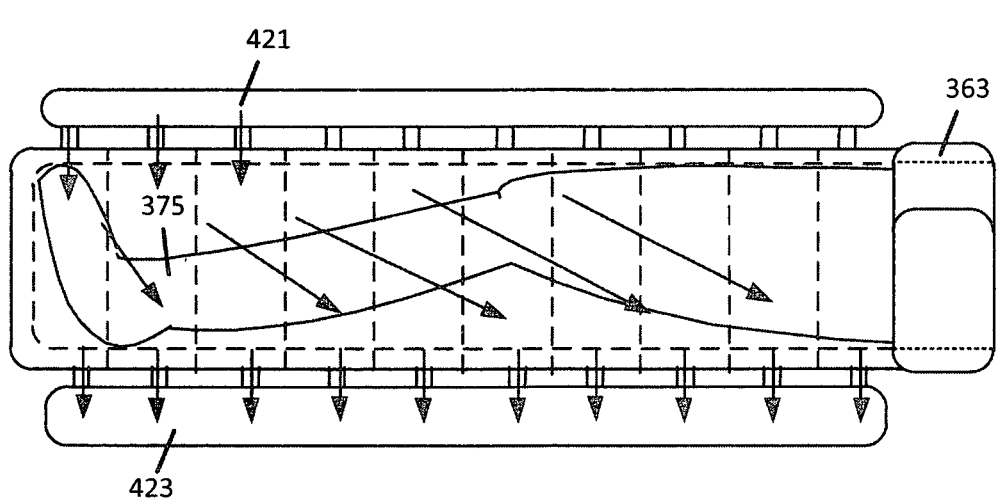
FIG. 74 illustrates a side view of an embodiment of a limb placed in a multi-bladder prep extremity bag with a fluid inlet manifold directing fluid through the distal fluid inlets.

In the example illustrated in FIG. 74, the inlet manifold 421 can direct the clean gas through the inlet ports over the foot and ankle into the prep extremity bag 360 from the inlet manifold 421. Because the gas flows away from the foot and ankle, the sterilization fluid moves away from the foot/ankle portion of the limb minimizing the chances that any contaminants may flow towards the foot or knee. Residual cleaning solution and drying gases can flow into the outlets and into the outlet fluid manifold 423.

Figure 75:
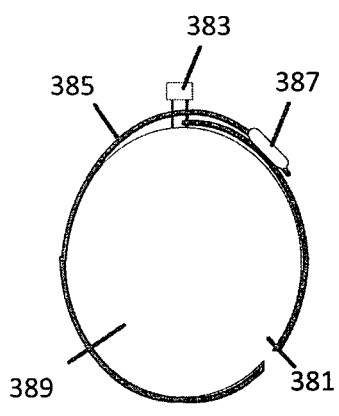
FIGS. 75-77 illustrate a front view of a tourniquet having a bladder and a tension strap.
Figure 76:
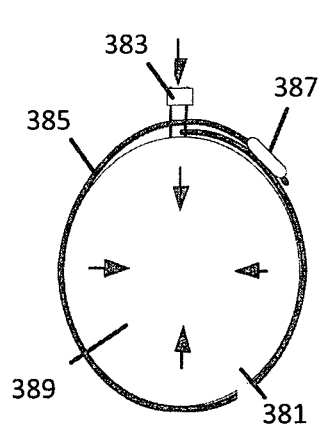
Figure 77:
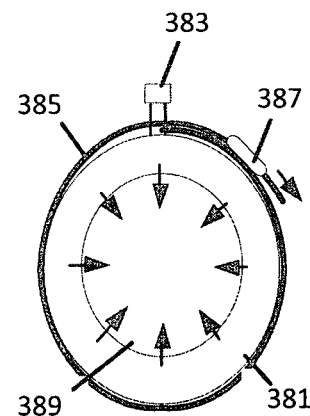

With reference to FIGS. 75-77, a front view of a first embodiment of a tourniquet that can be used with the described prep extremity bag is illustrated. The tourniquets can have an annular bladder 381, a gas valve 383 and a supplemental compression mechanism. In the illustrated example, the compression mechanism is a strap 385 coupled to a ratchet mechanism 387. With reference to FIG. 75, a limb 389 can be placed within the annular bladder 381. The inner surfaces of the bladder 381 can have an adhesive the sticks to the outer circumference of the limb 389 and creates a seal against the limb 389. With reference to FIG. 76, pressurized gas is injected through the gas valve 383 to compress the bladder 381 against the limb 389. Once the desired pressure is reached, the gas valve 383 is closed. With reference to FIG. 77, the ratchet 387 can be actuated to contract the strap 385 to further compress the tourniquet around the limb 389.

Figure 78:
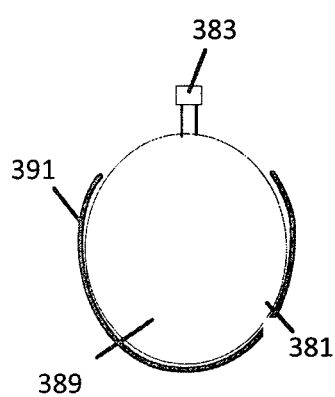
FIGS. 78-80 illustrate a front view of a tourniquet having a bladder and an elastic strap tension mechanism.
Figure 79:
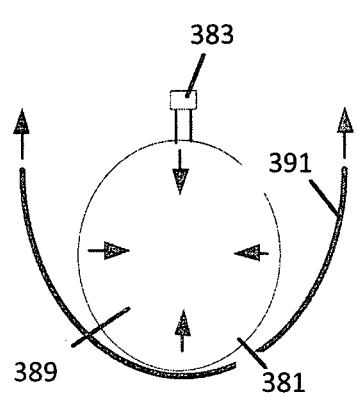
Figure 80:
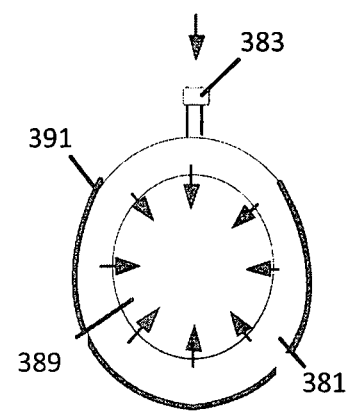

With reference to FIGS. 78-80, a front view of a second embodiment of a tourniquet that can be used with the described prep extremity bag is illustrated. With reference to FIG. 78, a limb 389 can be placed within the annular bladder 381. The inner surfaces of the bladder 381 can have an adhesive the sticks to the outer circumference of the limb 389 and creates a seal against the limb 389. With reference to FIG. 79, an elastic strap 391 attached to an outer surface of the bladder 381 can be tensioned. The inner surface of the strap 391 can have a coupling mechanism that can secure the strap 391 to the outer surface of the bladder 381. Examples of coupling mechanisms include hook and loop couplings, adhesive couplings, mechanical fasteners, etc. This strap 391 tension can create a first compression force against the limb 389. With reference to FIG. 80, once the tensioned strap 391 is attached to the outer surface of the bladder 381, pressurized gas is injected through the gas valve 383 to further compress the bladder 381 against the limb 389. Once the desired pressure is reached, the gas valve 383 is closed.

Figure 81:
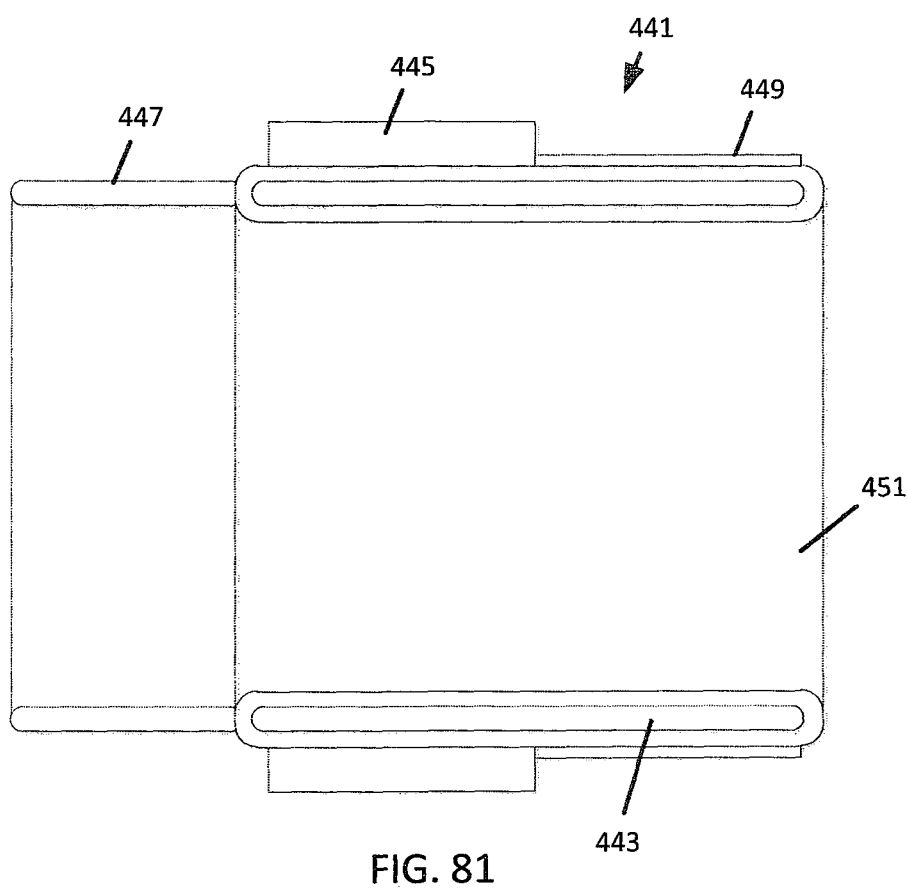
FIG. 81 illustrates a cross section side view of a modular tourniquet.

With reference to FIG. 81, a cross section side view of an embodiment of a tourniquet 441 is illustrated. In this embodiment the tourniquet 441 is a separate component that can be attached to a prep extremity bag and other drapes. The tourniquet 441 can have an annular bladder 443. The deflated tourniquet 441 can be placed over the limb of the patient. The inner surface 451 of the tourniquet 441 can have an adhesive that is secured to the skin of the limb. A coupling mechanism 447 can be attached to the annular bladder 443 which can be coupled to a prep extremity bag. For example in an embodiment, the coupling mechanism 447 can have a hook surface on the outer surface which can be coupled to a prep extremity bag having loop on a proximal inner surface. The tourniquet 441 can be placed around the limb and then the prep extremity bag can be placed over the limb with the inner circumference having a loop surface being attached to the hook surface on the outer circumference of the coupling mechanism 447. In other embodiments, any other coupling mechanism can be used to secure the tourniquet 441 coupling mechanism 447 to the prep extremity bag. The tourniquet 441 can also have a drape coupling mechanism 449 which can allow drapes to be secured to the tourniquet 441. The drapes can extend over a torso of a patient. In an embodiment, the drape coupling mechanism 449 can be a loop material that can be attached to a hook material on an edge portion of a drape. In other embodiments, any other coupling mechanism can be used to attach the drapes to the tourniquet 441. The tourniquet 441 can be placed around a limb and the bladder 443 can be inflated to compress the tourniquet 441 against a limb. The tourniquet 441 may also include a band 445 that can be tightened or tensioned to further compress the tourniquet 441 against the limb.

In an embodiment, a specific procedure can be performed to use the inventive pre-tourniquet system. The tourniquet 441 can be applied to the limb but not tightened. A mechanism should be used to prevent the movement of the tourniquet 441 relative to the limb. For example, an adhesive can be applied to the inner surface of the tourniquet 441 to secure the limb and prevent movement of the tourniquet 441 over the surface of the limb. In another embodiment, an adhesive tape such as double sided tape can be applied to the circumference of the limb at the contact area with the tourniquet 441. Once the tourniquet 441 is secured to the limb, the tourniquet 441 can be tightened around the limb and then the bladder 443 can be inflated to further compress the tourniquet 441 against the limb. The drapes can be attached to the tourniquet 441 as described above.

Figure 82:
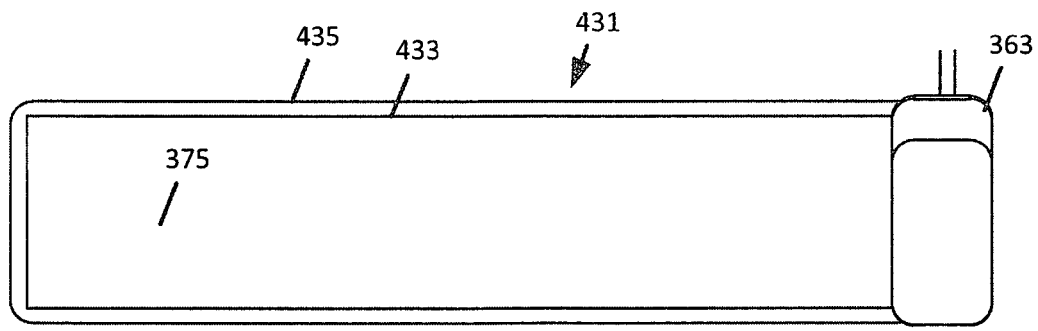
FIG. 82 illustrates a side view of a limb of a prep extremity bag having integrated drapes.
Figure 83:
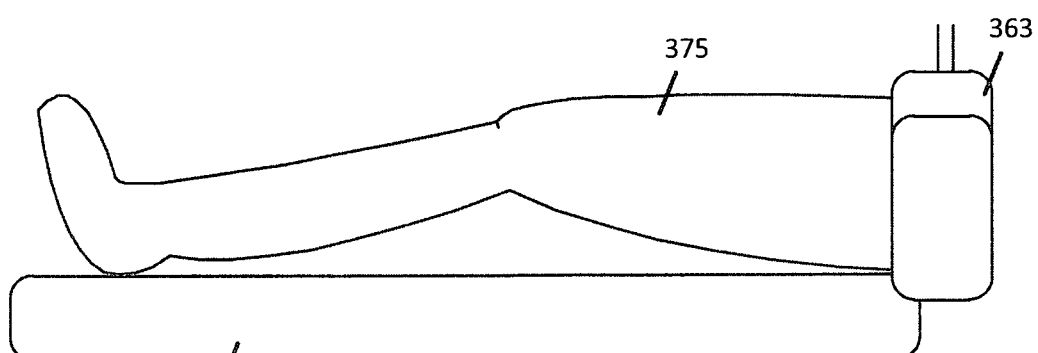
FIG. 83 illustrates a side view of a limb of a prep extremity bag having an inte grated drape deployed under the limb.
Figure 84:
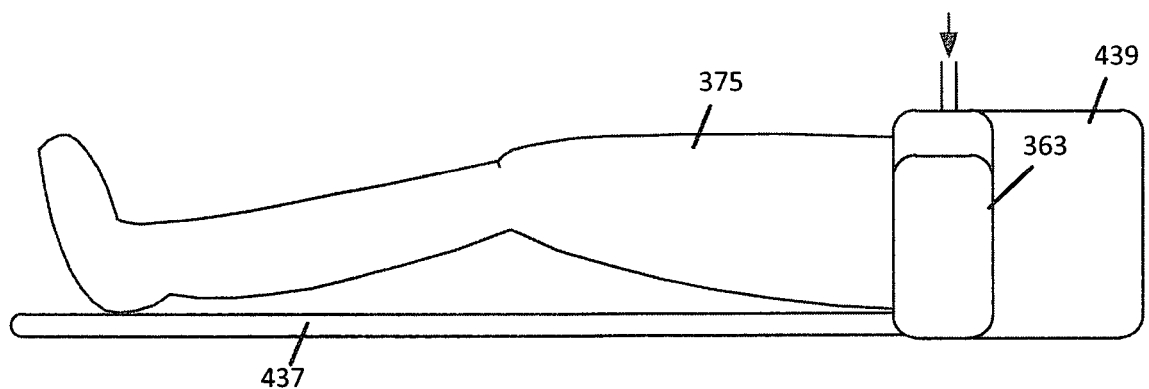
FIG. 84 illustrates a side view of a limb of a prep extremity bag having deployed drapes over the torso.

In yet another embodiment, the prep extremity bag 431 can have integrated drapes. With reference to FIG. 82, in an embodiment the limb 375 is placed in the prep extremity bag 360 and the tourniquet 363 is secured to the limb 375. The prep extremity bag 431 can have an inner bag 433 that contains the cleaning fluid and an outer bag 435 that contains the drapes. The limb 375 can then be sterilized and dried within the prep extremity bag 431 as described above outside the operating room. The patient and sterilized limb 375 can then be moved into the operating room. With reference to FIG. 83, the prep extremity bag 431 can be opened and the inner bag can be removed. The lower drapes 437 contained within the outer bag can be expanded outward from the limb 375 with the limb 375 resting on the drape 437. With reference to FIG. 84, pressurizing a bladder as described above can compress the tourniquet 363 against the limb 375 to reduce blood flow through the limb 375 during the surgical procedure. In addition to the lower drapes 437, the tourniquet 363 can also include an upper drape 439 that extends proximally over the abdomen of the patient.

Figure 85:
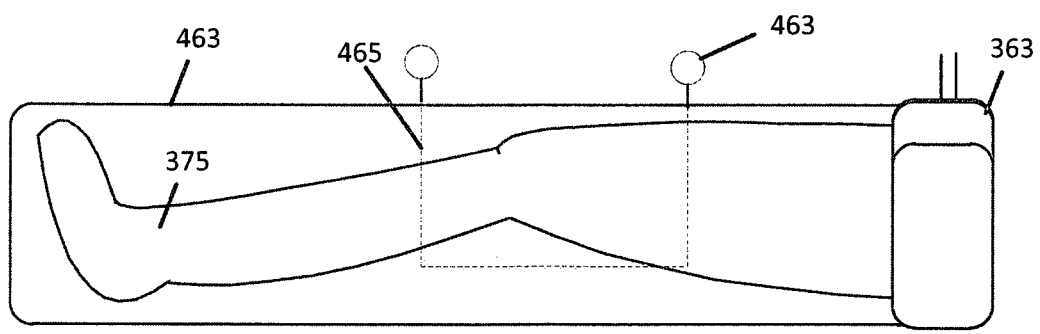
FIG. 85 illustrates a prep extremity bag having pull tabs for opening the bag.
Figure 86:
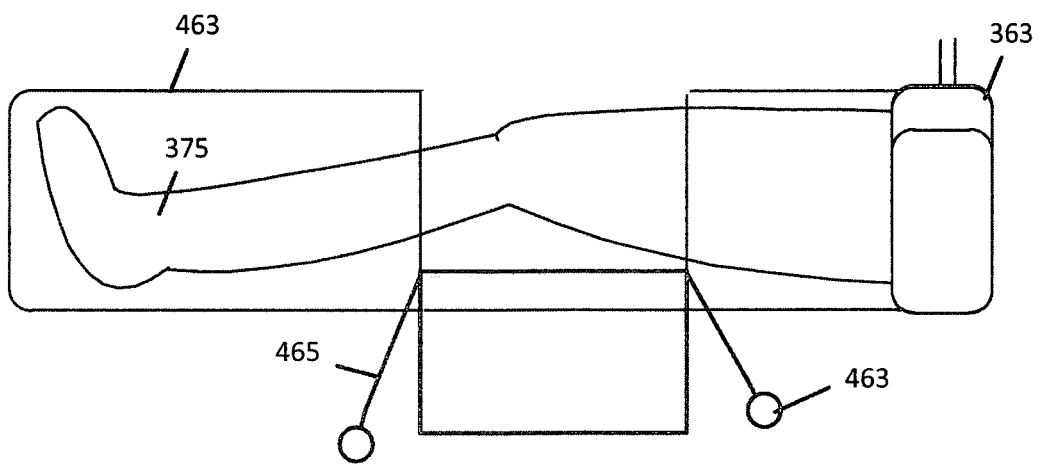
FIG. 86 illustrates a prep extremity bag having pull tabs pulled and an opened bag.

As discussed above with reference to FIG. 71, in different embodiments, a prep extremity bag can be used to sterilize a limb and then opened to allow access the limb for surgical procedures. In an embodiment, the prep extremity bag can have a mechanism to open specific portions of the prep extremity bag. With reference to FIG. 85, in an embodiment, a limb 375 can be placed in a prep extremity bag 461 and sterilized. The prep extremity bag 461 can include pull tabs 463 can be attached to lines 465 which can cut portions of the prep extremity bag 461. With reference to FIG. 86, after the limb 375 is sterilized, the user can then pull the pull-tabs 463 to open a portion of the prep extremity bag 461. In the illustrated example, the pull-tabs 463 are pulled to cause the lines 465 to open the designated portions of the prep extremity bag 463. Portions of the prep extremity bag 461 between the lines 465 can extend away from the limb 375. In other embodiments, any other suitable mechanism can be used to open and/or cut portions of the prep extremity bag 463.

Figure 87:
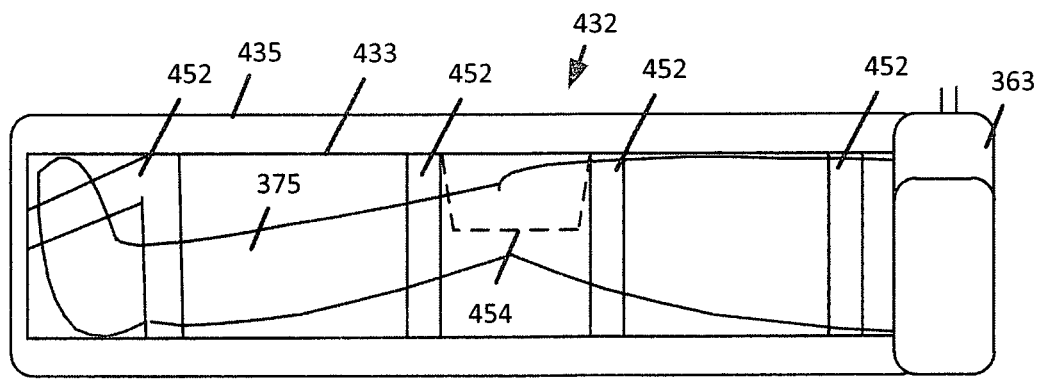
FIG. 87 illustrates a side views of an embodiment limb placed in a multi-layer prep extremity bag.
Figure 88:
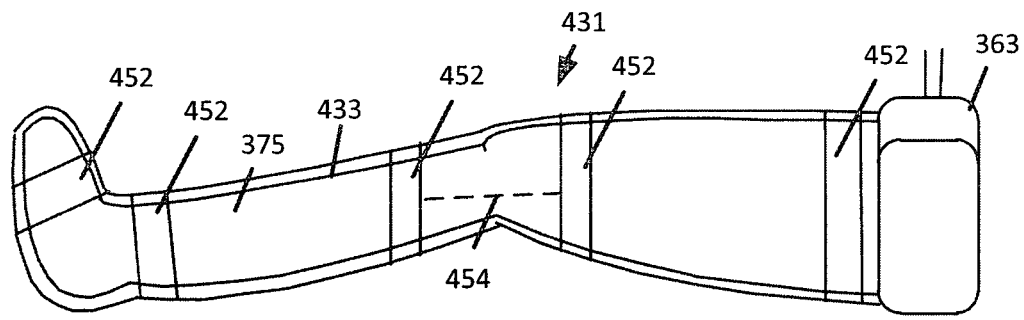
FIG. 88 illustrates a side views of an embodiment limb placed in a prep extremity bag with the outer layer removed.
Figure 89:
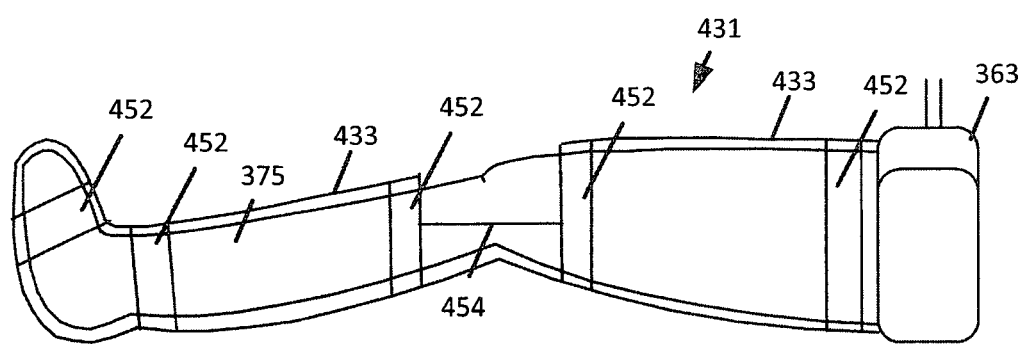
FIG. 89 illustrates a side views of an embodiment limb placed in a prep extremity bag with a portion of the inner layer opened.
Figure 90:
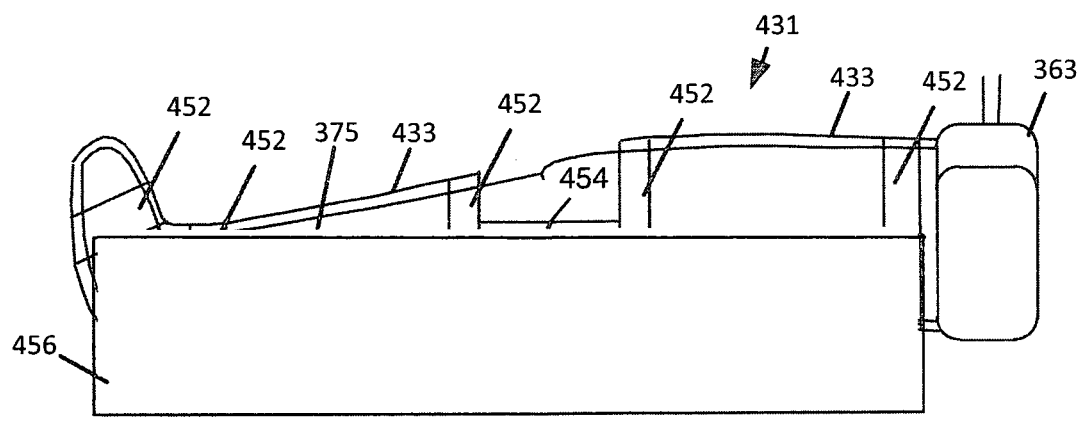
FIG. 90 illustrates a side views of an embodiment limb placed in a prep extremity bag with drapes attached to the inner layer.

With reference to FIG. 87, in an embodiment, the prep extremity bag 432 can have one or more bands or tabs 452 attached to the inner bag 433 and perforations 454 formed in the inner bag 433 and an outer bag 435 surrounding the inner bag 433. The limb 375 can be sterilized and dried in any manner described above. The bands or tabs 452 can be devices that can secure the inner bag 433 to the limb 375 such as elastic tape, adhesive tape, etc. that can have fasteners such as hook and loop closures to secure the bands or tabs 452 around the limb 375. With reference to FIG. 88, once the leg 375 can be dried, the outer bag can be removed and the inner bag 433 can be pressed against the leg 375. The bands or tabs 452 can be used to secure the inner bag 433 to the leg 375. With reference to FIG. 89, the patient can be moved to the OR and the knee portion of the inner bag 433 can be opened along the perforations 454. With reference to FIG. 90, drapes 456 can be attached to the inner bag 433 adjacent to the perforations 454 in the inner bag 433.

Figure 91:
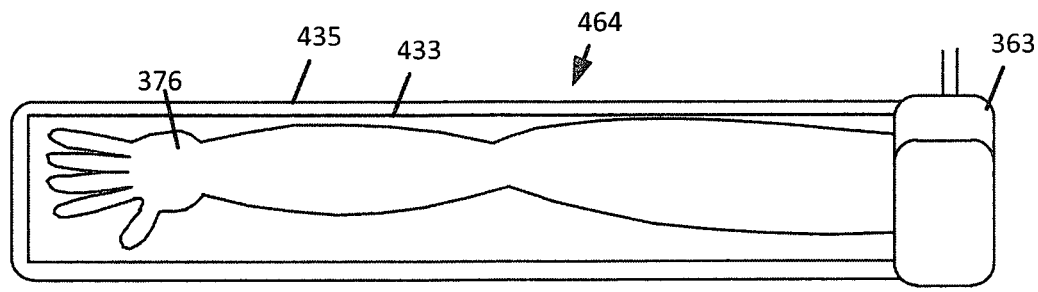
FIG. 91 illustrates a side view of an embodiment an arm placed in a prep extremity bag.

Although the figures illustrate embodiments for legs, in other embodiments, the bag can be used with arms, hips and shoulders. With reference to FIG. 91, an arm 376 can be used with the inventive prep extremity bag 464. The arm 376 can be placed in the prep extremity bag 464 and the tourniquet can be sealed against the arm 376. The tourniquet 464 is not tightened. The cleaning fluid can be placed between the arm 376 and the inner bag 433. Gas pressure can be applied between the inner bag 433 and the outer bag 435 to compress the inner bag 433 against the arm 376 in any of the cyclical manners described above. In an embodiment, the sterilization process is substantially automated. After the arm 376 is cleaned, the cleaning fluid is drained from the inner bag 433. Drying gas can then be directed into the inner bag 433 to dry the arm. When the patient is moved into the OR, the tourniquet 363 can be tightened to reduce blood flow and the limb can be elevated. The inner bag 433 and the outer bag 435 can be cut open and the surgery can be performed on the arm 376. Once the operation is completed, the tourniquet 363 can be released and blood flow can be restored to the arm 376.

Figure 92:
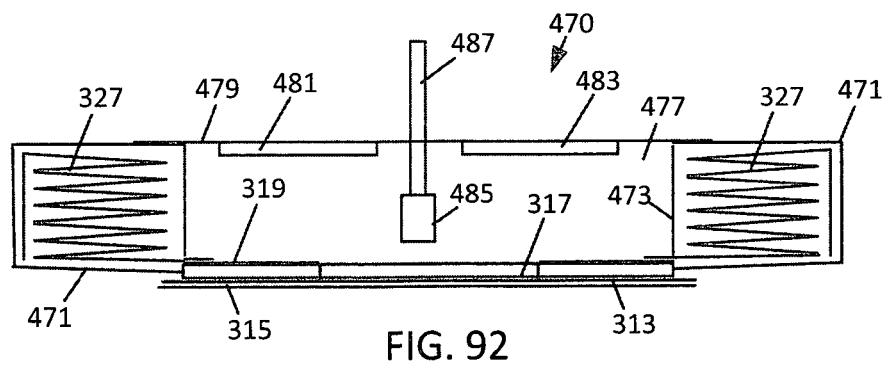
FIG. 92 illustrates a side view of pre-drape apparatus with integrated sheets.

With reference to FIG. 92, in an embodiment, the pre-drape apparatus 470 can include compressed drapes 327 that are in a sterile drape package 471 and skin cleaning components within a sterile volume 477 that is placed over an incision area of the patient. The pre-drape apparatus 470 includes a boundary layer 319 that is a structural material having a lower adhesive layer 313 that is attached to a release layer 315. A compressed perimeter (folded in this example) drape 327 is attached to the perimeter boundary layer 319 that can be folded in a compact accordion manner. The sterile drape package 471 covers the draped sections 327 and is attached to the boundary layer 319. The sterile drape package 471 can have an inner wall 473 that separates the compressed drapes 327 from the sterile volume 477.

The sterile volume 477 can have an upper area defined by a cover 479 that can be attached to upper surfaces of the sterile drape package 471 and a lower area that is defined by the boundary layer 319. The boundary layer 319 can have an aperture 317 that is placed over the incision site. A cleaning tool 487 can have a handle that extends through the cover 479 that can be manipulated through the cover 479 without compromising the sterile volume 477. A foam brush 485 can be attached to the bottom of the cleaning tool 487. A cleaning solution 481 and a numbing solution 483 can be stored in the sterile volume 477.

Figure 93:
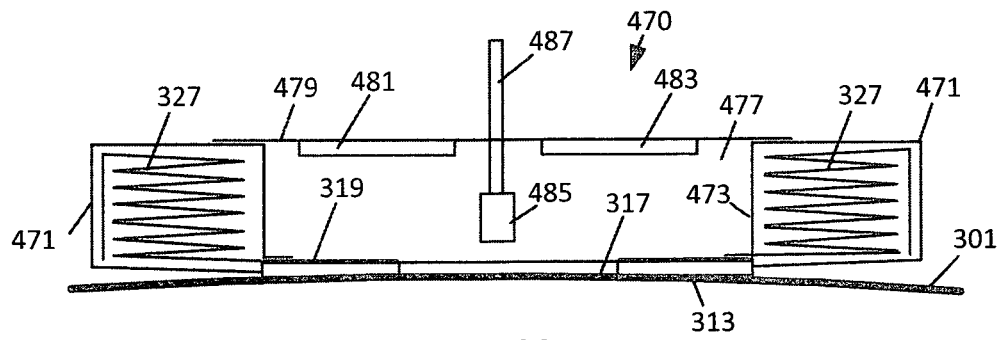
FIG. 93 illustrates a side view of pre-drape apparatus with integrated sheets on a patient.

With reference to FIG. 93, the lower release layer can be removed from the lower adhesive layer 313 and the lower adhesive layer 313 can be attached to the skin 301 of the patient. The boundary layer 319 can include an aperture 317 that can be positioned over a surgical incision zone skin area. The cleaning solution 481 can be released into the sterile volume and the tool 487 can be used to move the brush 485 and the sterilization solution 481 against the skin 301 in the aperture 317. The sterilization solution can dry on the skin 301. Then the numbing solution 483 can be released into the sterile volume and the tool 487 can be used to move the brush 485 and the numbing solution 483 against the skin 301 in the aperture 317.

Figure 94:
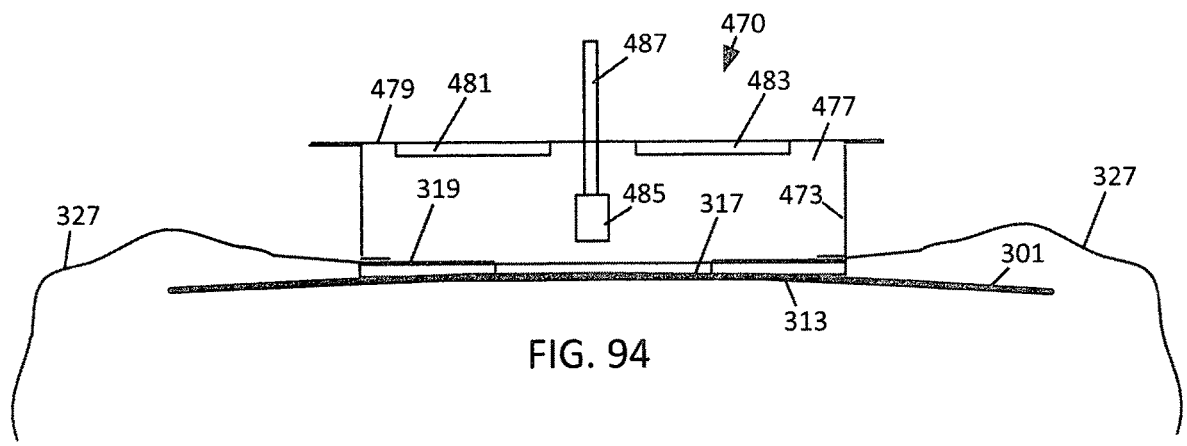
FIG. 94 illustrates a side view of pre-drape apparatus with sheets deployed on a patient.
Figure 95:
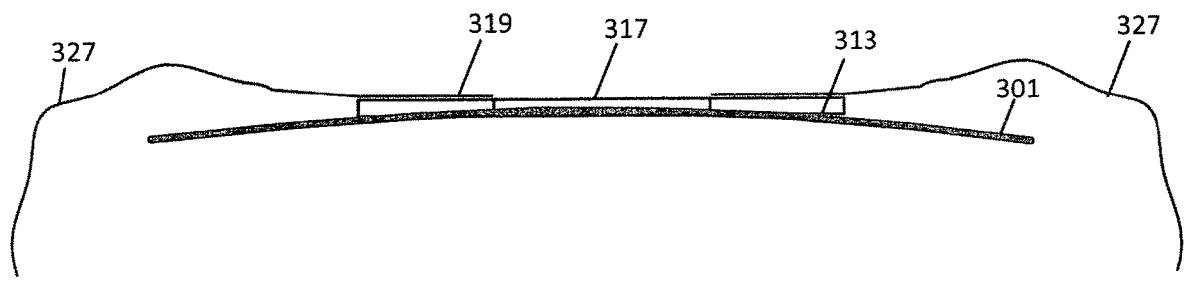
FIG. 95 illustrates a side view of pre-drape apparatus with sheets deployed on a patient.

In an embodiment, with reference to FIG. 94, the drape cover is opened in the OR, the folded sections 327 can be unfolded and expanded over the sides of the patient's skin 301. The cover 479 and the walls 473 can remain attached over the aperture 317 to maintain the sterility of the aperture 317 as long as possible prior to the incision of the skin 301. With reference to FIG. 95, when the folded sections 327 have been fully expanded, the aperture cover 318 and the walls 473 can be removed to expose the aperture 317 in the OR. The described process can simplify and speed the preparation of the patient prior to the surgical incision.

It will be understood that the inventive system has been described with reference to particular embodiments; however additions, deletions and changes could be made to these embodiments without departing from the scope of the inventive system. Although the systems that have been described include various components, it is well understood that these components and the described configuration can be modified and rearranged in various other configurations.

The invention claimed is:
1. A method for using a pre-drape apparatus comprising:
providing the pre-drape apparatus having: a drape having a lower surface and an upper surface, a first adhesive layer attached a lower surface of the drape, an upper cover and a lower cover attached to the upper cover wherein the upper cover and the lower cover contain the drape and the adhesive layer in a sterile volume;

sterilizing an area of skin over an incision area outside an operating room;

removing the lower cover from the upper cover outside an operating room;

attaching the first adhesive layer of the drape to the area of skin outside an operating room wherein the drape is positioned over the incision area;

removing the upper cover within the operating room.

2. The method for using the pre-drape apparatus of claim 1 further comprising:

providing a perimeter portion of the drape surrounding the drape attached to the skin of the patient; and expanding the perimeter portion of the drape outward from the drape attached in the skin of the patient in the operating room.

3. The method for using the pre-drape apparatus of claim 2 wherein the perimeter portion of the drape is expanded by unrolling or unfolding.

4. The method for using the pre-drape apparatus of claim 3 further comprising:

providing a sterilization fluid and a prep space cover drape attached to the upper surface of the drape; and expanding the prep space cover drape to create a space between the incision area and the prep space cover drape outside the operating room;

wherein the sterilizing the area of skin over the incision area is performed with the sterilization fluid.

5. The method for using the pre-drape apparatus of claim 1 further comprising:

a fenestration in a portion of the drape attached to the skin over the incision area.

6. The method for using the pre-drape apparatus of claim 1 further comprising:

providing a numbing fluid and a prep space cover drape attached to the upper surface of the drape;

expanding the prep space cover drape to create a space between the incision area and the prep space cover drape outside the operating room; and numbing the incision area with the numbing fluid.

7. The method for using the pre-drape apparatus of claim 1 further comprising:

providing a frame attached to the lower cover in a compressed state; and erecting the frame to create a volume above the incision area outside the operating room.

8. A method for using a pre-drape apparatus comprising:

providing the pre-drape apparatus having: a lower drape having a lower surface and an upper surface, a first adhesive layer attached a lower surface of the lower drape, an upper cover and a lower cover attached to the upper cover wherein the upper cover and the lower cover contain the lower drape and the adhesive layer in a sterile volume;

sterilizing an area of skin over an incision area outside an operating room;

removing the lower cover from the upper cover outside an operating room;

attaching the first adhesive layer of the lower drape to the area of skin outside an operating room wherein a fenestration portion of the lower drape is positioned over the incision area;

removing the upper cover within the operating room.

9. The method for using the pre-drape apparatus of claim 8 further comprising:

providing an upper drape attached to the upper surface of the lower drape with a second adhesive layer wherein a first adhesive force of the first adhesive layer is greater than a second adhesive force of the second adhesive layer; and removing the upper drape from the lower drape before the lower drape is removed from the area of skin.

10. The method for using the pre-drape apparatus of claim 1 further comprising:

providing an upper drape having an expandable drape portion attached to the upper surface of the lower drape with a second adhesive layer; and expanding the expandable drape portion outward from the lower drape in the operating room.

11. The method for using the pre-drape apparatus of claim 8 further comprising:

providing a sterilization fluid and a prep space cover drape attached to the upper surface of the lower drape; and expanding the prep space cover drape to create a space between the incision area and the prep space cover drape outside the operating room;

wherein the sterilizing the area of skin over the incision area is performed with the sterilization fluid.

12. The method for using the pre-drape apparatus of claim 8 further comprising:

providing a numbing fluid and a prep space cover drape attached to the upper surface of the lower drape;

expanding the prep space cover drape to create a space between the incision area and the prep space cover drape outside the operating room; and numbing the incision area with the numbing fluid.

13. The method for using the pre-drape apparatus of claim 8 further comprising:

providing a frame attached to the lower cover in a compressed state; and erecting the frame to create a volume above the incision area outside the operating room.

* * * * *